(12) United States Patent
Song et al.

(10) Patent No.: US 11,551,785 B2
(45) Date of Patent: Jan. 10, 2023

(54) GENE SEQUENCING DATA COMPRESSION PREPROCESSING, COMPRESSION AND DECOMPRESSION METHOD, SYSTEM, AND COMPUTER-READABLE MEDIUM

(71) Applicant: GENETALKS BIO-TECH (CHANGSHA) CO., LTD., Hunan (CN)

(72) Inventors: Zhuo Song, Hunan (CN); Gen Li, Hunan (CN); Pengxia Liu, Hunan (CN); Zhenguo Wang, Hunan (CN); Bolun Feng, Hunan (CN)

(73) Assignee: GENETALKS BIO-TECH (CHANGSHA) CO., LTD., Hunan (CN)

( * ) Notice: Subject to any disclaimer, the term of this patent is extended or adjusted under 35 U.S.C. 154(b) by 691 days.

(21) Appl. No.: 16/618,404

(22) PCT Filed: Sep. 18, 2018

(86) PCT No.: PCT/CN2018/106192
§ 371 (c)(1),
(2) Date: Dec. 2, 2019

(87) PCT Pub. No.: WO2019/076177
PCT Pub. Date: Apr. 25, 2019

(65) Prior Publication Data
US 2020/0185058 A1    Jun. 11, 2020

(30) Foreign Application Priority Data

Oct. 20, 2017  (CN) .......................... 201710982649.1
Oct. 20, 2017  (CN) .......................... 201710982666.5
Oct. 20, 2017  (CN) .......................... 201710982696.6

(51) Int. Cl.
*G06F 16/22* (2019.01)
*G16B 30/00* (2019.01)
(Continued)

(52) U.S. Cl.
CPC ......... *G16B 30/00* (2019.02); *G06F 16/1744* (2019.01); *G06F 16/2228* (2019.01); *G06F 16/2455* (2019.01); *G16B 20/00* (2019.02)

(58) Field of Classification Search
CPC ............. G06F 16/2228; G06F 16/2455; G06F 16/1744
See application file for complete search history.

(56) References Cited

U.S. PATENT DOCUMENTS 6,141,657 A * 10/2000 Rothberg ............... C12N 15/10
                                                                      435/6.12
8,847,799 B1 * 9/2014 Kennedy ............... G16B 50/50
                                                                      341/87
(Continued)

FOREIGN PATENT DOCUMENTS

CN        103699818       4/2014
CN        104699998       6/2015
(Continued)

OTHER PUBLICATIONS

"International Search Report (Form PCT/ISA/210) of PCT/CN2018/106192", dated Nov. 20, 2018, with English translation thereof, pp. 1-4.

Primary Examiner — Eliyah S. Harper
(74) Attorney, Agent, or Firm — JCIP Global Inc.

(57) ABSTRACT

The present invention discloses a gene sequencing data compression preprocessing, compression and decompression method, a system, and a computer-readable medium. The preprocessing method implementation steps include: obtaining reference genome data; obtaining a mapping relationship between a short string K-mer and a prediction (Continued)

character c to obtain a prediction data model P1 containing any short string K-mer in the positive strand and negative strand of a reference genome and the prediction character c in a corresponding adjacent bit. The compression and decompression methods relate to performing compression/decompression on the basis of the prediction data model P1. The system is a computer system including a program for executing the previous method. The computer-readable medium includes a computer program for executing the previous method. The present invention can be oriented towards lossless gene sequencing data compression, provides fully effective information for a high-performance lossless compression and decompression algorithm for gene sequencing data.

26 Claims, 3 Drawing Sheets

(51) Int. Cl.
  *G06F 16/2455* (2019.01)
  *G06F 16/174* (2019.01)
  *G16B 20/00* (2019.01)

(56) References Cited

U.S. PATENT DOCUMENTS

| | | | |
|---|---|---|---|
| 9,275,059 B1 * | 3/2016 | Vijendra | G16B 50/30 |
| 2004/0053246 A1 * | 3/2004 | Sorenson | G16B 30/00 |
| | | | 435/6.1 |
| 2016/0292198 A1 * | 10/2016 | Karten | G16B 50/00 |
| 2016/0306919 A1 * | 10/2016 | Ding | G16B 30/10 |
| 2017/0147597 A1 * | 5/2017 | Leighton | G16B 30/10 |
| 2017/0185712 A1 * | 6/2017 | Karten | G06F 16/24568 |
| 2017/0357665 A1 * | 12/2017 | Olivares-Amaya | G16B 50/00 |
| 2018/0101547 A1 * | 4/2018 | Greenfield | G06F 16/2228 |

FOREIGN PATENT DOCUMENTS

| | | |
|---|---|---|
| CN | 105631239 | 6/2016 |
| CN | 106021985 | 10/2016 |
| CN | 106603591 | 4/2017 |

* cited by examiner

GENE SEQUENCING DATA COMPRESSION PREPROCESSING, COMPRESSION AND DECOMPRESSION METHOD, SYSTEM, AND COMPUTER-READABLE MEDIUM

CROSS-REFERENCE TO RELATED APPLICATION

This application is a 371 of international application of PCT application serial no. PCT/CN2018/106192, filed on Sep. 18, 2018, which claims the priority benefit of China application no. 201710982649.1, filed on Oct. 20, 2017, China application no. 201710982666.5, filed on Oct. 20, 2017 and China application no. 201710982696.6, filed on Oct. 20, 2017. The entirety of each of the above mentioned patent applications is hereby incorporated by reference herein and made a part of this specification.

TECHNICAL FIELD

The present invention relates to gene sequencing and data compression technologies, in particular to a gene sequencing data compression preprocessing, compression and decompression method, a system, and a computer-readable medium.

BACKGROUND

As next generation sequence (NGS) keeps unfolding in recent years, gene sequencing is fast in speed and low in cost. Moreover, the gene sequencing technology has been extensively popularized and applied in various fields of biology, medicine, heath, criminal investigation, agriculture, etc., which leads to the explosive growth in original gene sequencing data at 3~5 times every year, even faster. Besides, every gene sequencing sample is very big, for example, one person's 55×whole genome sequencing data is about 400 GB. Hence, there are technology and cost challenges for storage, management, retrieval and transmission of massive gene testing data.

Data compression is one of technologies to mitigate this challenge. Also, it is a process of converting data to be more compact than original format data to decrease the storage space. Original input data comprises a symbol sequence to be compressed or reduced. These symbols are coded by a compressor and output as coded data. At some later time point, the coded data is generally input into a decompressor to be decoded and rebuilt, and then the original data is output in a symbol sequence way. If the output data is always identical to the input data completely, this compression scheme is lossless, also called a lossless encoder. Otherwise, it is a lossy compression scheme.

At present, researchers from various countries in the world have developed various gene sequencing data compression methods. Based on applications thereof, the gene sequencing data compressed must be rebuilt and restored to be original data whenever possible. Hence, the gene sequencing data compression methods with actual meanings refer to lossless compression. In case of classifying based on the total technical route, the gene sequencing data compression method may be divided into general-purpose, reference-based and reference-free compression algorithms.

The general-purpose compression algorithm is to compress data without considering the features of gene sequencing data.

The reference-free compression algorithm is to directly compress target sample data by using a compression method without using reference genome based on the features of the gene sequencing data. The common compression method of the existing reference-free compression algorithm includes Huffman coding compression algorithm, dictionary method represented by LZ77 and LZ78, arithmetic coding compression algorithm, and other basic compression algorithms and their variant and optimization compression algorithms.

The reference-based compression algorithm comprises the steps of selecting a certain genome data as a reference genome, and indirectly compressing data using features of the gene sequencing data and the similarity between target sample data and reference genome data. Common similarity representation, coding and compression methods of the existing reference-based compression algorithms mainly comprise Huffman coding compression algorithm, dictionary method represented by LZ77 and LZ78, arithmetic coding compression algorithm, and other basic compression algorithms and their variant and optimization compression algorithms.

Two most common technical indicators for measuring compression algorithm performances or efficiencies comprise compression ratio or compression rate; compression/decompression time or compression/decompression speed. Compression ratio=(data size after compression/data size before compression)×100%, compression rate (data size before compression/data size after compression), namely, the compression ratio and the compression rate are the inverse of each other. The compression ratio and compression rate are only in connection with the compression algorithms which can be compared with each other directly, showing better algorithm performance or efficiency when the compression ratio is lower or the compression rate is higher; the compression/decompression time means machine running time required from original data reading to decompression; the compression/decompression speed means data volume that can be processed every unit time averagely. The compression/decompression time and the compression/decompression speed are relevant to the compression algorithm and the used machine environment (including hardware and system software). As a result of this, the compression/decompression time or compression/decompression speeds of various algorithms must be meaningful based on the same machine environment. It is on this premise that the algorithm performance or efficiency is better when the compression/decompression time is shorter and the compression/decompression speed is faster. Besides, an additional reference technical indicator is resource consumption at runtime, mainly a peak value stored by machines. When the compression ratio and compression/decompression time are equivalent, the less storage requirements indicate the better algorithm performance or efficiency.

The comparative research results of the existing gene sequencing data compression methods made by the researchers indicate that the general-purpose, reference-free and reference-based compression algorithms have the following problems: 1. the compression ratio can be further decreased; 2. when the relatively better compression ratio is obtained, the algorithm compression/decompression time is relatively long, which makes the time cost become a new problem. Besides, compared with the general-purpose and reference-free compression algorithms, the reference-based compression algorithm can generally obtain the better compression ratio. However, for the reference-based compression algorithm, the choice of the reference genome will result in the algorithm performance stability problem, namely, when different reference genomes are selected to process the same target sample data, there may be obvious differences in compression algorithm performance; when the same reference genome selection strategies are applied to processing same and different gene sequencing sample data, there may be obvious differences in compression algorithm performances as well. To be specific, for the reference-based compression algorithm, how to preprocess to improve the compression ratio and compression performance of the gene sequencing data based on the reference genome has been an urgent technical problem to be solved.

SUMMARY

The technical problem to be solved by the present invention is: for the above problem of the prior art, the present invention first provides a gene sequencing data compression preprocessing method, system and computer-readable medium. The present invention can face the preprocessing method of reference genome data compressed from lossless gene sequencing data, provide full and effective information for high performance lossless compression and decompression algorithm, and can predict the prediction character c in the adjacent bit of the short string K-mer in any genome data sample through detecting the prediction data model P1 containing any short string K-mer in a positive strand and a negative strand of the reference genome and the prediction character c in the corresponding adjacent bit; if the prediction information is more accurate, a lower compression ratio can be achieved for the genome data sample. Next, the present invention further provides a gene sequencing data compression method, system and computer-readable medium; the gene sequencing data compression method of the present invention is a lossless, reference-based gene sequencing data compression method, and has the advantages of low compression ratio, short compression time and stable compression performance; gene data does not need to be accurately compared, and accordingly a higher computing efficiency is obtained. If the prediction accuracy of the prediction data model P1 is higher, there are more repeated character strings in the reversible computing result, and the compression ratio is lower. Then, the present invention further provides a gene sequencing data decompression method, system and computer-readable medium; the gene sequencing data decompression method pf the present invention is a lossless, reference-based gene sequencing data decompression method, and has the advantages of low compression ratio, short decompression time and stable decompression performance; gene data does not need to be accurately compared, and accordingly a higher computing efficiency is obtained. If the prediction accuracy of the prediction data model P1 is higher, there are more repeated character strings in the reversible computing result, and the compression ratio is lower.

To solve the above technical problem, the technical solution applied by the present invention is as follows:

On one hand, the present invention provides a gene sequencing data compression preprocessing method, comprising the following implementation steps:

1) obtaining reference genome data ($data_{ref}$);

2) obtaining a mapping relation between any fixed length substring as the short string K-mer in the reference genome data ($data_{ref}$) and the prediction character c thereof, so as to obtain a prediction data model P1 including any short string K-mer in the positive and negative strands of the reference genome and the prediction character c at the corresponding adjacent bit thereof.

Preferably, step 2) comprises the following implementation steps:

2.1) sequentially extracting a fixed length substring in the positive strand S1 of the reference genome data ($data_{ref}$) as the short string K-mer to construct a positive strand short string set KS1 according to the designated space, wherein the positive strand S1 is the reference genome data ($data_{ref}$) of the original sequence;

2.2) sequentially extracting a fixed length substring in the negative strand S2 of the reference genome data ($data_{ref}$) as the short string K-mer to construct a negative strand short string set KS2 according to the designated space, wherein the negative strand S2 is the negative sequence complementary gene sequence of the reference genome data ($data_{ref}$), and between the negative sequence complementary gene sequence and the reference genome data ($data_{ref}$), the bases A and T are interchanged, and the base C and G are interchanged;

2.3) generating the prediction data model P1 corresponding to the reference genome data ($data_{ref}$) according to the positive strand short string set KS1 and negative strand short string set KS2, wherein the prediction data model P1 contains the mapping relation between any short string K-mer in positive strand S1 and negative strand S2 and the prediction character c in the most possible adjacent bit obtained from statistics.

Preferably, step 2.3) comprises the following detailed steps:

2.3.1) with respect to the positive strand short string set KS1, sequentially extracting the short string K-mer and constructing positive strand prediction set KP1, wherein every element in the positive strand short string set KS1 has one corresponding tuple in the positive strand prediction set KP1, and the tuple at least contains three types of information: short string K-mer, mark d from the positive strand, and the base letter $c_0$ in the adjacent bit of the positive strand S1;

2.3.2) with respect to the negative strand short string set KS2, sequentially extracting the short string K-mer and constructing negative strand prediction set KP2, wherein every element in the negative strand short string set KS2 has one corresponding tuple in the negative strand prediction set KP2, and the tuple at least contains three types of information: short string K-mer, mark d from the negative strand, and the base letter $c_0$ of the element in the adjacent bit of the negative strand S2;

2.3.3) mapping the tuples in the positive strand prediction set KP1 and negative strand prediction set KP2 to the base letters A, C, G, T, counting any short string K-mer in the positive strand S1 and negative strand S2 and the base letters in the most possible adjacent bits obtained from statistics, obtaining the prediction data model P1 containing any short string K-mer in positive strand and negative strand of the reference genome and the prediction data model P1 of the prediction character c in the corresponding adjacent bit.

Preferably, step 2.3.3) comprises the following detailed steps:

2.3.3.1) taking out every tuple (k-mer, d, $c_0$) one by one from the positive strand prediction set KP1 and the negative strand prediction set KP2, wherein k-mer is the short string K-mer corresponding to the tuple, d is the type of positive and negative strands, d=0 indicates the positive strand, d=1 indicates the positive strand, $c_0$ is the base letter of the adjacent bit corresponding to the short string K-mer of the corresponding tuple in the positive strand S1 or the negative strand S2;

2.3.3.2) using a preset mapping function to map a sub-tuple (k-mer, d) of every tuple (k-mer, d, $c_0$) taken out to a certain line of the integer set in a range of [0, L] so as to generate a 2D statistical table F containing L lines and 4 columns, and determining a corresponding line of a hit line of a corresponding base letter $c_0$ of the corresponding adjacent bit in the positive strand S1 or the negative strand S2 by virtue of the short string K-mer corresponding to the tuple in the tuple (k-mer, d, $c_0$), wherein L is a supremum of the integer set, and 0 is an infimum of the integer set; the number of base letters A, C, G, T corresponding to every value in the integer set and 4 columns of corresponding base letters A, C, G and T in the 2D statistical table F are counted; an element $F_{i,c}$ in the 2D statistical table F stores the number of the base letters A, C, G, T corresponding to the sub-tuple (k-mer, d) with a value of i, in which a subscript i∈[0, L], c∈{A, C, G and T};

2.3.3.3) traversing the 2D statistical table F from lines 0 to L, constructing the base letters corresponding to the element $F_{i,c}$ with the maximum value in every line to be a 1D character sequence as a prediction data model P1 containing any short string K-mer in the positive strand and negative strand of the reference genome and the prediction character c of the corresponding adjacent bit, wherein the length of the prediction data model P1 is L, L is the supremum of the integer set, the i(th) character P1[i] of the prediction data model P1 indicates the prediction character c of the short string K-mer corresponding to the tuple in the i(th) line of the integer set.

Preferably, step 2.3.3.2) of counting the number of A, C, G, T corresponding to every value in the integer set specifically refers to: when the sub-tuple (k-mer, d) of every tuple (k-mer, d, $c_0$) withdrawn is mapped to an integer set [0, L], with respect to four elements $F_{i,c}$ in every line of the 2D statistical table, four count values $F_{i,A}$, $F_{i,C}$, $F_{i,G}$, $F_{i,T}$ are set, respectively; if the base letter $c_0$ of the short string K-mer corresponding to the tuple in the i(th) line of the integer set in corresponding adjacent bit of the positive strand S1 or negative strand S2 is hit as A, $F_{i,A}$ in the i(th) line is plus 1; if the base letter $c_0$ of the short string K-mer corresponding to the tuple in the i(th) line of the integer set in corresponding adjacent bit of the positive strand S1 or negative strand S2 is hit as C, $F_{i,C}$ in the i(th) line is plus 1; if the base letter $c_0$ of the short string K-mer corresponding to the tuple in the i(th) line of the integer set in corresponding adjacent bit of the positive strand S1 or negative strand S2 is hit as G, $F_{i,G}$ in the i(th) line is plus 1; if the base letter $c_0$ of the short string K-mer corresponding to the tuple in the i(th) line of the integer set in corresponding adjacent bit of the positive strand S1 or negative strand S2 is hit as T, $F_{i,T}$ in the i(th) line is plus 1; finally the numbers $F_{i,A}$, $F_{i,C}$, $F_{i,G}$, $F_{i,T}$ of A, C, G, T corresponding to every value in the integer set are obtained.

Preferably, step 2.3) comprises the following detailed steps:

S2.3.1) with respect to the positive strand short string set KS1, sequentially extracting the short string K-mer and constructing positive strand prediction set KP1, so that every element in the positive strand short string set KS1 has one corresponding tuple in the positive strand prediction set KP1, and the tuple at least contains three types of information: short string K-mer, mark d from the positive strand, and the base letter $c_0$ in the adjacent bit of the positive strand S1;

S2.3.2) with respect to the negative strand short string set KS2 sequence, extracting the short string K-mer and constructing negative strand prediction set KP2, so that every element in the negative strand short string set KS2 has one corresponding tuple in the negative strand prediction set KP2, and the tuple at least contains three types of information: short string K-mer, mark d from the negative strand, and the base letter $c_0$ in the adjacent bit of the negative strand S2;

S2.3.3) generating a training set by the short strings K-mer corresponding to the tuples in a positive strand prediction set KP1 and a negative strand prediction set KP2 and a base letter co corresponding to the adjacent bit in the positive strand S1 or the negative strand S2 thereof, training a neural network model by the training set, and taking the trained neural network mode as the prediction data model P1 containing any short string K-mer in positive strand and negative strand of the reference genome and the prediction data model P1 of the prediction character c in the corresponding adjacent bit.

Meanwhile, the present invention further provides a gene sequencing data compression preprocessing system based on character prediction, comprising a computer system, wherein the computer system is programmed to perform the steps of the aforesaid gene sequencing data compression preprocessing method.

Besides, the present invention further provides a computer-readable medium, on which a computer program is stored, wherein the computer program allows the computer system to perform the steps of the aforesaid gene sequencing data compression preprocessing method of the present invention.

On one hand, the present invention provides a gene sequencing data compression method, including the following implementation steps:

1) traversing a gene sequencing data sample (data) to obtain a read sequence R with a length of Lr bit;

2) with respect to every read sequence R, selecting the original gene letter in k bit as the original gene character string $CS_0$, generating k bit character string with fixed length based on the length of k bit as the sliding window sequence from the original gene character string $CS_0$, as short string K-mer, determining a type d of positive and negative strands of the read sequence R based on the short string K-mer, and obtaining a prediction character c in the adjacent bit corresponding to every short string K-mer through the preset prediction data model P1 to obtain a prediction character set PS with a length of Lr−k bit, wherein the prediction data model P1 contains any short string K-mer in the positive and negative strands of the reference genome and a prediction character c in corresponding adjacent bit; performing reversible computing by the reversible function after coding the Lr−k bit original gene letter and the prediction character set PS exclusive of k bit original gene letter in the read sequence R, wherein the output computing results coded by any pair of same characters are identical by virtue of the reversible function; compressing and outputting the type d of the positive and negative strands of the read sequence R, k bit original gene letter and reversible computing result, as three data flows.

Preferably, step 2) comprises the following implementation steps:

2.1) traversing a read sequence R with a length of Lr from the gene sequencing data sample (data), with respect to the read sequence R, selecting k bit original gene letter as the original gene character string $CS_0$, generating fixed length substring based on the k bit length as the sliding window sequence from the original gene character string $CS_0$, as the short string K-mer, and obtaining the read sequence short string set KR;

2.2) generating fixed length substring as the short string K-mer according to the sequence, determining a type d of positive and negative strands of the read sequence R based on the short string K-mer, and obtaining a prediction character c in corresponding adjacent bit of every short string K-mer to obtain a prediction character set PS with a length of Lr−k bit through a preset prediction data model P1, wherein the prediction data model P1 contains any short string K-mer in the positive and negative strands of the reference genome and a prediction character c thereof in the corresponding adjacent bit;

2.3) performing reversible computing by the reversible function after coding the Lr−k bit original gene letter and the prediction character set PS exclusive of k bit original gene letter in the read sequence R, wherein the output computing results coded by any pair of same characters are identical by virtue of the reversible function;

2.4) compressing and outputting the type d of the positive and negative strands of the read sequence R, the original gene character string $CS_0$ and reversible computing result, as three data flows;

2.5) judging whether the read sequence R in the gene sequencing data sample (data) is traversed, if not, jumping to step 2.1); otherwise ending and exiting.

Preferably, step 2.2) comprises the detailed steps:

2.2.1) sequentially extracting a short string K-mer with respect to the read sequence short string set KR, constructing a positive strand prediction sequence KP1 based on the short string K-mer, wherein any short string K-mer in a read sequence short string set KR has a corresponding tuple (k-mer, 0) in the positive strand prediction sequence KP1, k-mer is the short string K-mer, and 0 indicates supposing the short string K-mer from the positive strand;

2.2.2) obtaining the prediction character c corresponding to every tuple (k-mer, 0) in the positive strand prediction sequence KP1 through the prediction data model P1, so as to obtain a positive strand prediction character sequence PS1 formed by all prediction characters c; the prediction data model P1 contains any short string K-mer in the positive and negative strands of the reference genome and a prediction character c corresponding to the adjacent bit thereof;

2.2.3) sequentially extracting a short string K-mer with respect to the read sequence short string set KR, constructing a negative strand prediction sequence KP2 based on the short string K-mer, wherein any short string K-mer in the read sequence short string set KR has a corresponding tuple (k-mer, 1) in the negative strand prediction sequence KP2, k-mer is the short string K-mer, and 1 indicates supposing the short string K-mer from the negative strand;

2.2.4) obtaining the prediction character c corresponding to the adjacent bit through the prediction data model P1 with respect to every tuple (k-mer, 1) in the negative strand prediction sequence KP2, and obtaining the negative strand prediction character sequence PS2 formed by all prediction characters c;

2.2.5) calculating an editing distance L1 between the positive strand prediction character sequence PS1 and Lr−k bit original gene letter exclusive of k bit original gene letter in the read sequence R, calculating an editing distance L2 between the negative strand prediction character sequence PS2 and the Lr−k bit original gene letter exclusive of k bit original gene letter in the read sequence R;

2.2.6) judging whether the editing distance L1 is less than L2, if yes, determining the type d of the positive and negative strands of the read sequence R to be a positive strand, and the positive strand prediction character sequence PS1 to be the prediction character set PS in Lr−k bit; otherwise, determining the type d of the positive and negative strands of the read sequence R to be negative strand, and the negative strand prediction character sequence PS2 to be the prediction character set PS in Lr−k bit.

Preferably, the prediction data model P1 is a gene character string with a length of L. Step 2.2.2) of obtaining the prediction character c in the adjacent bit thereof corresponding to every tuple (k-mer, 0) in the positive strand prediction sequence KP1 through the prediction data model P1 comprises the following detailed steps:

2.2.2.1) mapping every tuple (k-mer, 0) in the positive strand prediction sequence KP1 to a certain line of an integer set [0, L] using a mapping function corresponding to the prediction data model P1, wherein L is a supremum of the integer set which is as long as the prediction data model P1, and 0 is an infimum of the integer set; generating a one-dimensional (1D) table T1 with a length of (Lr−k+1) according to a mapping result, wherein the i(th) element T1[i] in the 1D table T1 is respectively and sequentially stored and mapped to a value of the mapping function corresponding to the tuple (k-mer, 0) in the i(th) line of the integer set, $i \in [0, Lr-k]$;

2.2.2.2) obtaining a prediction character c corresponding to the adjacent bit from the prediction data model P1 according to the value of the mapping function corresponding to each tuple of 1D table T1, and generating 1D character sequence PS1, so that the i(th) PS1[i] value of the 1D character sequence PS1 is equal to the i(th) character P1[T1[i]] in the prediction data model P1, and the i(th) character P1[T1[i]] in the prediction data model P1 is the corresponding character c with the mapping function value of PS1[i] corresponding to the tuple (k-mer, 0), wherein $i \in [0, Lr-k]$, Lr is a read length of the read sequence R, and k is the length of the short string K-mer.

Preferably, step 2.2.4) of obtaining the prediction character c in the adjacent bit thereof corresponding to every tuple (k-mer, 1) in the negative strand prediction sequence KP2 through the prediction data model P1 comprises the following detailed steps:

2.2.4.1) mapping every tuple (k-mer, 1) in the negative strand prediction sequence KP2 to a certain line of an integer set [0, L] using the mapping function corresponding to the prediction data model P1, wherein L is a supremum of the integer set which is as long as the prediction data model P1, and 0 is an infimum of the integer set; generating a 1D table T2 with a length of (Lr−k+1) according to a mapping result, wherein the i(th) element T2[i] in the 1D table T2 is respectively and sequentially stored and mapped to a value of the mapping function corresponding to the tuple (k-mer, 1) in the i(th) line of the integer set, $i \in [0, Lr-k]$;

2.2.4.2) obtaining the prediction character c corresponding to the adjacent bit thereof from the prediction data model P1 thereof according to the value of the mapping function corresponding to each tuple (k-mer, 1) in the 1D table T2, and generating the 1D character sequence PS2, so that the i(th) PS2[i] value of the 1D character sequence PS2 is equal to an i(th) character P1[T2[i]] in the prediction data model P1, wherein the i(th) character P1[T2[i]] in the prediction data model P1 is the corresponding prediction character c with a mapping function value of PS2[i] corresponding to the tuple (k-mer, 0), $i \in [0, Lr-k]$, Lr is a read length of the read sequence R, and k is the length of the short string K-mer.

Preferably, the prediction data model P1 is the neural network model which is trained in advance based on the short string K-mer in the reference genome and the corresponding base letter $c_0$ in the adjacent bit thereof; step 2.2.2) of obtaining the prediction character c in the adjacent bit thereof corresponding to every tuple (k-mer, 0) in the positive strand prediction sequence KP1 through the mapping function of the prediction data model P1 specifically refers to inputting every tuple (k-mer, 0) in the positive strand prediction sequence KP1 into the neural network model to obtain the prediction character c corresponding to the tuple (k-mer, 0); step 2.2.4) of obtaining the prediction character c in the adjacent bit thereof corresponding to every tuple (k-mer, 1) in the negative strand prediction sequence KP2 through the prediction data model P1 specifically refers to inputting every tuple (k-mer, 1) in the negative strand prediction sequence KP2 into the neural network model to obtain the prediction character c corresponding to the tuple (k-mer, 1).

Preferably, an XOR function or bit subtraction function is specifically applied for the reversible function in step 2).

Preferably, compression in step 2) specifically refers to compression using a statistical model and entropy coding.

On the other hand, the present invention further provides a gene sequencing data compression system, comprising a computer system, wherein the computer system is programmed to perform the steps of the aforesaid gene sequencing data compression method of the present invention.

Besides, the present invention further provides a computer-readable medium on which a computer program is stored, wherein the computer program enables a computer to perform the steps of the aforesaid gene sequencing data compression method of the present invention.

On one hand, the present invention provides a gene sequencing data decompression method, comprising the following implementation steps:

1) traversing gene sequencing data ($data_c$) to be decompressed to obtain a read sequence $R_c$ to be decompressed;

2) with respect to every read sequence Rc to be decompressed, first decompressing and reconstructing the read sequence Rc to be decompressed as positive and negative strand type d, original gene sequence CS1 ink bit and reversible computing result CS2 with a length of Lr−k bit; taking the original gene sequence CS1 in the k bit as the initial short string K-mer, and obtaining the corresponding prediction character c in the adjacent bit of the short string K-mer through the preset prediction data model P1, P1, wherein the prediction data model P1 contains any short string K-mer in the positive and negative strands of the reference genome and the corresponding prediction character c in the adjacent bit thereof; when one prediction character c is obtained, forming a new short string K-mer constituted by new prediction character c and the last k-1 bit of the short string K-mer, obtaining the new prediction character c by the preset prediction data model P1, and eventually obtaining the prediction character set PS with a length of Lr−k bit constituted by all prediction characters c; performing the reverse computing for the coded reversible computing result CS2 and the prediction character set PS to obtain the decrypted result of the reversible computing result CS2 in the Lr−k bit by virtue of the inverse function of the reversible function; combining the decrypted results of the original gene sequence CS1 in the k bit and the reversible computing result CS2 to obtain the original read sequence R corresponding to the read sequence Rc to be decompressed, and outputting the original read sequence R.

Preferably, step 2) comprises the following detailed steps:

2.1) traversing gene sequencing data ($data_c$) to be decompressed to obtain the read sequence $R_c$ to be decompressed;

2.2) decompressing and reconstructing the read sequence $R_c$ to be decompressed to be the positive and negative strands type d, the original gene sequence CS1 in the k bit and the reversible computing result CS2 with the length of Lr−k bit;

2.3) taking the original gene sequence CS1 in the k bit as the initial short string K-mer, and obtaining the corresponding prediction character c in the adjacent bit of the short string K-mer through the preset prediction data model P1, wherein the prediction data model P1 contains any short string K-mer in the positive and negative strands of the reference genome and the corresponding prediction character c in the adjacent bit thereof; when one prediction character c is obtained, forming a new short string K-mer constituted by new prediction character c and the last k-1 bit of the short string K-mer, obtaining the new prediction character c by the preset prediction data model P1, and eventually obtaining the prediction character set PS with a length of Lr−k bit constituted by all prediction characters c;

2.4) performing the reverse computing for the coded reversible computing result CS2 and the prediction character set PS to obtain the decrypted result of the reversible computing result CS2 in the Lr−k bit by virtue of the inverse function of the reversible function;

2.5) combining the decrypted results of the original gene sequence CS1 in the k bit and the reversible computing result CS2 to obtain the original read sequence R corresponding to the read sequence $R_c$ to be decompressed, and outputting the original read sequence R;

2.6) judging whether the read sequence $R_c$ to be decompressed in the gene sequencing data sample ($data_c$) to be decompressed is traversed, if not, jumping to step 2.1); otherwise ending and exiting.

Preferably, step 2.3) comprises the following detailed steps:

2.3.1) creating a window variable CS and a prediction character set PS corresponding to the short string K-mer, setting the initial value of the window variable CS as the original gene sequence CS1 in the k bit, creating an iteration variable j and setting the initial value as 0;

2.3.2) constructing the window variable CS, the type d of positive and negative strands of the read sequence Re to be decompressed into a tuple (CS, d), mapping the tuple (CS, d) into an integer set [0, 1] by the mapping function, wherein L is the supremum of the integer set and equal to the length of the prediction data model P1; 0 is the infimum of the integer set, and the prediction data model P1 contains any short string K-mer in the positive and negative strands of the reference genome and a prediction character c thereof corresponding to the adjacent bit;

2.3.3) querying the i(th) P1[i] in the prediction data model P1 with the function value obtained from the mapping function, as the prediction character c corresponding to the adjacent bit of the window variable CS, wherein i∈[0, L]; assigning the prediction character c to the j(th) bit in the prediction character set PS, wherein j∈[0, Lr−k], and Lr−k is the length of reversible computing result CS2.

2.3.4) after combining the last k-1 bit of the window variable CS and the prediction character c obtained currently, assigning to the window variable CS, and adding 1 to the iteration variable j;

2.3.5) judging whether the iteration variable j is greater than the length (Lr−k) of the reversible computing result CS2, if yes, jumping to the next step, otherwise, jumping to step 2.3.2);

2.3.6) outputting the prediction character set PS with the length of (Lr−k).

Preferably, step 2.3) comprises the following detailed steps:

S2.3.1) creating a window variable CS and a prediction character set PS corresponding to the short string K-mer, setting the initial value of the window variable CS as the original gene sequence CS1 in the k bit, creating an iteration variable j and setting the initial value as 0;

S2.3.2) inputting the window variable CS to the prediction data model P1 to obtain the prediction character c of the short string K-mer corresponding to the adjacent bit in the positive strand and negative strand of the reference genome, wherein the prediction data model P1 is the neural network model which is trained in advance based on the short string K-mer in the reference genome and the base element $c_0$ corresponding to the adjacent bit thereof;

S2.3.3) assigning the prediction character c to the j(th) bit in the prediction character set PS, wherein j∈[0, Lr−k], and Lr−k is the length of reversible computing result CS2.

S2.3.4) after combining the last k-1 bit of the window variable CS and the prediction character c obtained currently, assigning to the window variable CS, and adding 1 to the iteration variable j;

S2.3.5) judging whether the iteration variable j is greater than the length (Lr−k) of the reversible computing result CS2, if yes, jumping to the next step, otherwise, jumping to step 2.3.2);

S2.3.6) outputting the prediction character set PS with the length of (Lr−k).

Preferably, the reversible function specifically refers to an XOR function or a bit subtraction function. An inverse function of the XOR function is the XOR operation, and an inverse function of the bit subtraction function is a bit addition function.

Preferably, decompression and reconstruction in step 2) specifically refer to decompression and reconstruction using inverse algorithms of a statistical model and entropy coding.

On the other hand, the present invention further provides a gene sequencing data decompression system based on character prediction, comprising a computer system, wherein the computer system is programmed to perform the steps of the aforesaid gene sequencing data decompression method of the present invention.

Besides, the present invention further provides a computer-readable medium, on which a computer program is stored, wherein the computer program allows the computer to perform the steps of the aforesaid gene sequencing data decompression method of the present invention.

The gene sequencing data compression preprocessing method of the present invention has the following advantages: The present invention can extract the information related to the reference genome and generate prediction database, in order to provide full, effective information which can be queried and facilitates calculation for subsequent high performance lossless compression and decompression algorithm of gene sequencing data based on reference genome. The present invention can predict the prediction character c of the short string K-mer in the adjacent bit of any genome data sample, and the reversible computing by the reversible function (for example, XOR or bit subtraction) based on prediction character c and the original character can change the correct prediction bit into the same character. Based on the basic principle of compression algorithm, the more the same characters are, the lower the implemented compression ratio will be. For this, the more accurate the prediction information of the gene sequencing data compression preprocessing method of the present invention is, the lower the compression ratio of the genome data sample will be.

The gene sequencing data compression method of the present invention has the following advantages:

1. The gene sequencing data compression method of the present invention is a lossless, reference-based gene sequencing data compression method, capable of effectively promoting the compression ratio of gene sequencing data by using the prediction data model P1 of the reference genome, and has the advantages of low compression ratio, short compression time and stable compression performance.

2. Different from using the reference sequence for precise comparison for the gene sequences and then performing data compression in the prior art, the present invention does not need to accurately compare gene data, and accordingly a higher computing efficiency is obtained. If the prediction accuracy of the prediction data model P1 is higher, there are more repeated character strings in the reversible computing result, and the compression ratio is lower.

The gene sequencing data decompression method of the present invention has the following advantages:

1. The present invention is a lossless, reference-based gene sequencing data decompression method, capable of effectively promoting the compression ratio of gene sequencing data by using the prediction data model P1 of the reference genome, and has the advantages of low compression ratio, short decompression short and stable decompression performance.

2. Different from using the reference sequence for precise comparison for the gene sequences and then performing data compression in the prior art, the present invention does not need to accurately compare gene data, and accordingly a higher computing efficiency is obtained. If the prediction accuracy of the prediction data model P1 is higher, there are more repeated character strings in the reversible computing result, and the compression ratio is lower.

DETAILED DESCRIPTION

I. With Respect to Gene Sequencing Data Compression Preprocessing Method of the Present Invention Embodiment 1.1

Figure 1:
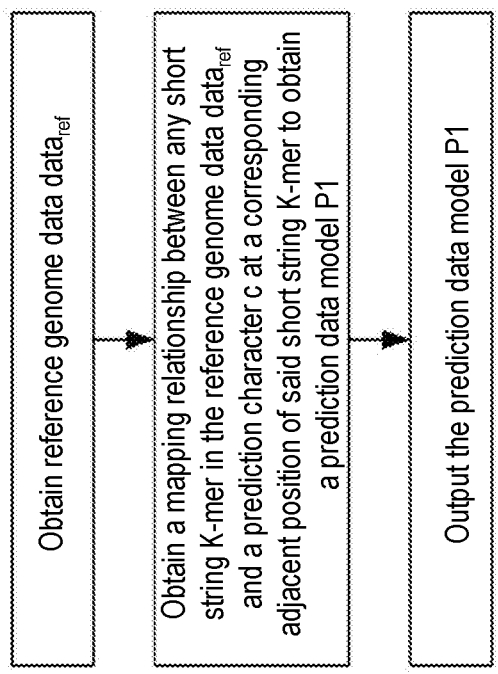
FIG. 1 is a basic flow diagram of the compression preprocessing method in embodiment 1.1 of the present invention.

As shown in FIG. 1, the gene sequencing data compression preprocessing method of this embodiment comprises the following implementation steps:

1) obtaining a reference genome data ($data_{ref}$) to be processed (the reference genome data ($data_{ref}$) is a gene sequence obtained by sequencing a certain specific individual complete or partial reference genome of one or a plurality of species);

2) obtaining a mapping relation between any fixed length substring as the short string K-mer in the reference genome data ($data_{ref}$) and the prediction character c thereof, so as to obtain a prediction data model P1 including any short string K-mer in the positive and negative strands of the reference genome and the prediction character c of the corresponding adjacent bit thereof. The length k of the short string K-mer is generally valued as a specific value between 16 and 32.

It should be noted that, the adjacent bit may refer to the next bit or/and last bit: if the short string K-mer is extracted from the first K characters during gene sequencing data compression, the adjacent bit specifically refers to the next bit; on the contrary, if the short string K-mer is extracted from the last k characters during gene sequencing data compression, the adjacent bit specifically refers to the last bit; the short string K-mer is extracted from the middle k characters during gene sequencing data compression, the adjacent bit needs to both contain the next bit and the last bit.

In this embodiment, step 2) comprises the following implementation steps:

2.1) sequentially extracting a fixed length substring in the positive strand S1 of the reference genome data (data$_{ref}$) as the short string K-mer to construct a positive strand short string set KS1 according to the designated space, wherein the positive strand S1 is the reference genome data (data$_{ref}$) of the original sequence;

2.2) sequentially extracting a fixed length substring in the negative strand S2 of the reference genome data (data$_{ref}$) as the short string K-mer to construct a negative strand short string set KS2 according to the designated space, wherein the negative strand S2 is the negative sequence complementary gene sequence of the reference genome data (data$_{ref}$), and between the negative sequence complementary gene sequence and the reference genome data (data$_{ref}$), the bases A and T are interchanged, and the base C and G are interchanged;

2.3) generating the prediction data model P1 corresponding to the reference genome data (data$_{ref}$) according to the positive strand short string set KS1 and negative strand short string set KS2, wherein the prediction data model P1 contains the mapping relation between any short string K-mer in positive strand S1 and negative strand S2 and the prediction character c in the most possible adjacent bit obtained from statistics.

In this embodiment, step 2.3) comprises the following detailed steps:

2.3.1) with respect to the positive strand short string set KS1, sequentially extracting the short string K-mer and constructing positive strand prediction set KP1, wherein every element in the positive strand short string set KS1 has one corresponding tuple in the positive strand prediction set KP1, and the tuple at least contains three types of information: short string K-mer, mark d from the positive strand, and the base letter $c_0$ in the adjacent bit of the positive strand S1;

2.3.2) with respect to the negative strand short string set KS2, sequentially extracting the short string K-mer and constructing negative strand prediction set KP2, wherein every element in the negative strand short string set KS2 has one corresponding tuple in the negative strand prediction set KP2, and the tuple at least contains three types of information: short string K-mer, mark d from the negative strand, and the base letter $c_0$ of the element in the adjacent bit of the negative strand S2;

2.3.3) mapping the tuples in the positive strand prediction set KP1 and negative strand prediction set KP2 to the base letters A, C, G, T, counting any short string K-mer in the positive strand S1 and negative strand S2 and the base letters in the most possible adjacent bits obtained from statistics, obtaining the prediction data model P1 containing any short string K-mer in positive strand and negative strand of the reference genome and the prediction data model P1 of the prediction character c in the corresponding adjacent bit. In this embodiment, the type d of positive and negative strands is 0 or 1, wherein 0 represents that the read sequence R is from the positive strand, and 1 represents that the read sequence R is from the negative strand.

In this embodiment, step 2.3.3) comprises the following detailed steps:

2.3.3.1) taking out every tuple (k-mer, d, $c_0$) one by one from the positive strand prediction set KP1 and the negative strand prediction set KP2, wherein k-mer is the short string K-mer corresponding to the tuple, d is the type of positive and negative strands, d=0 indicates the positive strand, d=1 indicates the positive strand, $c_0$ is the base letter of the adjacent bit corresponding to the short string K-mer of the corresponding tuple in the positive strand S1 or the negative strand S2;

2.3.3.2) using a preset mapping function to map a sub-tuple (k-mer, d) of every tuple (k-mer, d, $c_0$) taken out to a certain line of the integer set in a range of [0, L] so as to generate a 2D statistical table F containing L lines and 4 columns, and determining a corresponding line of a hit line of a corresponding base letter $c_0$ of the corresponding adjacent bit in the positive strand S1 or the negative strand S2 by virtue of the short string K-mer corresponding to the tuple in the tuple (k-mer, d, $c_0$), wherein L is a supremum of the integer set, and 0 is an infimum of the integer set; the number of base letters A, C, G, T corresponding to every value in the integer set and 4 columns of corresponding base letters A, C, G and T in the 2D statistical table F are counted; an element $F_{i,c}$ in the 2D statistical table F stores the number of the base letters A, C, G, T corresponding to the sub-tuple (k-mer, d) with a value of i, in which a subscript i∈[0, L], c∈{A, C, G and T};

2.3.3.3) traversing the 2D statistical table F from lines 0 to L, constructing the base letters corresponding to the element $F_{i,c}$ with the maximum value in every line to be a 1D character sequence as a prediction data model P1 containing any short string K-mer in the positive strand and negative strand of the reference genome and the prediction character c of the corresponding adjacent bit, wherein the length of the prediction data model P1 is L, L is the supremum of the integer set, the i(th) character P1[i] of the prediction data model P1 indicates the prediction character c of the short string K-mer corresponding to the tuple in the i(th) line of the integer set.

It should be noted that, the length L of the prediction data model P1 involves the compression performance and compression ratio; if the length L of the prediction data model P1 is greater, the opportunity of generating a conflict is smaller and the prediction accuracy will be higher when the sub-tuple (k-mer, d) of every tuple (k-mer, d, $c_0$) withdrawn is mapped to a certain line in an integer set [0, L] to generate a 2D statistical table F with L lines and 4 columns, however, this may result in more computing consumption resources; on the contrary, if the length L of the prediction data model P1 is smaller, the opportunity of generating a conflict is greater, the prediction accuracy will be lower, and the computing consumption resources are fewer when the sub-tuple (k-mer, d) of every tuple (k-mer, d, $c_0$) withdrawn is mapped to a certain line in an integer set [0, L] to generate a 2D statistical table F with L lines and 4 columns.

In this embodiment, step 2.3.3.2) of counting the number of A, C, G, T corresponding to every value in the integer set specifically refers to: when the sub-tuple (k-mer, d) of every tuple (k-mer, d, $c_0$) withdrawn is mapped to an integer set [0, L], with respect to four elements $F_{i,c}$ in every line of the 2D statistical table, four count values $F_{i,A}$, $F_{i,C}$, $F_{i,G}$, $F_{i,T}$ are set, respectively; if the base letter $c_0$ of the short string K-mer corresponding to the tuple in the i(th) line of the integer set in corresponding adjacent bit of the positive strand S1 or negative strand S2 is hit as A, $F_{i,A}$ in the i(th) line is plus 1; if the base letter $c_0$ of the short string K-mer corresponding to the tuple in the i(th) line of the integer set in corresponding adjacent bit of the positive strand S1 or negative strand S2 is hit as C, $F_{i,C}$ in the i(th) line is plus 1; if the base letter $c_0$ of the short string K-mer corresponding to the tuple in the i(th) line of the integer set in corresponding adjacent bit of the positive strand S1 or negative strand S2 is hit as G, $F_{i,G}$ in the i(th) line is plus 1; the base letter $c_0$ of the short string K-mer corresponding to the tuple in the i(th) line of the integer set in corresponding adjacent bit of the positive strand S1 or negative strand S2 is hit as T, $F_{i,T}$ in the i(th) line is plus 1; finally the numbers $F_{i,A}$, $F_{i,C}$, $F_{i,G}$, $F_{i,T}$ of A, C, G, T corresponding to every value in the integer set are obtained.

As an application example of using the next bit as an adjacent bit, the prediction data model P1 obtained by the gene sequencing data compression preprocessing method of this embodiment is used for gene sequencing data compression, comprising the following steps:

A1) traversing a gene sequencing data sample (data) to obtain a read sequence R with a length of Lr;

A2) with respect to every read sequence R, generating a fixed length substring as short string K-mer according to the sequence, determining a type d of positive and negative strands of the read sequence R based on the short string K-mer, and obtaining a prediction character c corresponding to every short string K-mer to obtain a prediction character set PS with a length of Lr−k bit through a preset prediction data model P1, P1, wherein the prediction data model P1 contains any short string K-mer in the positive and negative strands of the reference genome and a corresponding next prediction character c thereof; performing reversible computing by the reversible function (for example XOR or bit subtraction) after coding the last Lr−k bit of the read sequence R and the prediction character set PS, wherein the output computing results coded by any pair of same characters are identical by virtue of the reversible function; compressing and outputting the type d of the positive and negative strands of the read sequence R (0 or 1 for the type d of the positive and negative strands, 0 represents that the read sequence R is from the positive strand, and 1 represents that the read sequence R is from the negative strand), first k bit and reversible computing result, as three data flows.

Step A2) comprises the following implementation steps:

A2.1) traversing the gene sequencing data sample (data) to obtain the read sequence R with the length of Lr bit, with respect to the read sequence R, generating a fixed length substring with the length of k according to the sequence, as short string K-mer, and obtaining the read sequence short string set KR;

A2.2) with respect to every short string K-mer of the read sequence short string set KR, determining a type d of positive and negative strands of the read sequence R based on the short string K-mer, and obtaining a prediction character c corresponding to every short string K-mer to obtain a prediction character set PS with a length of Lr−k bit through a preset prediction data model P1, wherein the prediction data model P1 contains any short string K-mer in the positive and negative strands of the reference genome and a corresponding next prediction character c thereof;

A2.3) coding a last Lr−k bit of the read sequence R and the prediction character set PS, and then performing reversible computing by means of a reversible function, wherein the output computing results coded by any pair of same characters are identical by virtue of the reversible function;

A2.4) compressing the type d of the positive and negative strands of the read sequence R, the first k bit and the reversible computing result that serve as three data streams, and outputting the compressed data streams;

A2.5) judging whether the read sequence R in the gene sequencing data sample (data) is traversed, if not, jumping to step A2.1); otherwise ending and exiting.

Step A2.2) comprises the following detailed steps:

A2.2.1) sequentially extracting a short string K-mer with respect to the read sequence short string set KR, constructing a positive strand prediction sequence KP1 based on the short string K-mer, wherein any short string K-mer in the read sequence short string set KR has a corresponding tuple (k-mer, 0) in the positive strand prediction sequence KP1, k-mer is the short string K-mer, and 0 indicates supposing the short string K-mer from the positive strand;

A2.2.2) obtaining the prediction character c corresponding to every tuple (k-mer, 0) in the positive strand prediction sequence KP1 through the prediction data model P1, P1, so as to obtain a positive strand prediction character sequence PS1 corresponding to the positive strand prediction sequence KP1; the prediction data model P1 contains any short string K-mer in the positive and negative strands of the reference genome and a corresponding prediction character c in the next bit thereof;

A2.2.3) sequentially extracting a short string K-mer with respect to the read sequence short string set KR, constructing a negative strand prediction sequence KP2 based on the short string K-mer, wherein any short string K-mer in the read sequence short string set KR has a corresponding tuple (k-mer, 1) in the negative strand prediction sequence KP2, k-mer is the short string K-mer, and 1 indicates supposing the short string K-mer from the negative strand;

A2.2.4) obtaining the prediction character c corresponding to every tuple (k-mer, 1) in the negative strand prediction sequence KP2 through the prediction data model P1 to obtain a negative strand prediction character sequence PS2 corresponding to the negative strand prediction sequence KP2;

A2.2.5) calculating an editing distance L1 between the positive strand prediction character sequence PS1 and a last Lr−k bit of the read sequence R, and an editing distance L2 between the negative strand prediction character sequence PS2 and the last Lr−k bit of the read sequence R;

A2.2.6) judging whether the editing distance L1 is less than L2, if yes, determining the type d of the positive and negative strands of the read sequence R to be a positive strand, and the positive strand prediction character sequence PS1 to be the prediction character set PS corresponding to the last Lr−k bit of the read sequence R; otherwise, determining the type d of the positive and negative strands of the read sequence R to be negative strand, and the negative strand prediction character sequence PS2 to be the prediction character set PS corresponding to the last Lr−k bit of the read sequence R.

The prediction data model P1 is a gene character string with a length of L. Step A2.2.2) of obtaining the prediction character c corresponding to every tuple (k-mer, 0) in the positive strand prediction sequence KP1 through the prediction data model P1 comprises the following detailed steps:

A2.2.2.1) mapping every tuple (k-mer,0) in the positive strand prediction sequence KP1 to a certain line of an integer set [0,L] using a mapping function corresponding to the prediction data model P1, P1, wherein L is a supremum of the integer set which is as long as the prediction data model P1, P1, and 0 is an infimum of the integer set; generating a one-dimensional (1D) table T1 with a length of (Lr−k+1) according to a mapping result, wherein the i(th) element T1[i] in the 1D table T1 is respectively and sequentially stored and mapped to a value of the mapping function corresponding to the tuple (k-mer, 0) in the i(th) line of the integer set, i∈[0, Lr−k];

A2.2.2.2) obtaining a corresponding prediction character c thereon from the prediction data model P1 according to the value of the mapping function corresponding to each tuple of 1D table T1, and generating 1D character sequence PS1, so that the i(th) PS1[$i$] value of the 1D character sequence PS1 is equal to the i(th) character P1[T1[i]] in the prediction data model P1, P1, and the i(th) character P1[T1[i]] in the prediction data model P1 is the corresponding character c with the mapping function value of PS1[i] corresponding to the tuple (k-mer, 0), wherein i∈[0, Lr−k], Lr is a read length of the read sequence R, and k is the length of the short string K-mer.

step A2.2.4) of obtaining the prediction character c corresponding to every tuple (k-mer, 1) in the negative strand prediction sequence KP2 through the prediction data model P1 comprises the following detailed steps:

A2.2.4.1) mapping every tuple (k-mer, 1) in the negative strand prediction sequence KP2 to a certain line of an integer set [0, L] using the mapping function corresponding to the prediction data model P1, P1, wherein L is a supremum of the integer set which is as long as the prediction data model P1, P1, and 0 is an infimum of the integer set; generating a 1D table T2 with a length of (Lr−k+1) according to a mapping result, wherein the i(th) element T2[i] in the 1D table T2 is respectively and sequentially stored and mapped to a value of the mapping function corresponding to the tuple (k-mer, 1) in the i(th) line of the integer set, i∈[0, Lr−k];

A2.2.4.2) obtaining the corresponding prediction character c from the prediction data model P1 thereof according to the value of the mapping function corresponding to each tuple (k-mer, 1) in the 1D table T2, and generating the 1D character sequence PS2, so that the i(th) PS2[i] value of the 1D character sequence PS2 is equal to an i(th) character P1[T2[i]] in the prediction data model P1, P1, wherein the i(th) character P1[T2[i]] in the prediction data model P1 is the corresponding prediction character c with a mapping function value of PS2[i] corresponding to the tuple (k-mer, 0), i∈[0, Lr−k], Lr is a read length of the read sequence R, and k is the length of the short string K-mer.

The reversible function in step A2) specifically refers to an XOR function. In this embodiment, A, C, G and T gene letters are respectively coded as 00, 01, 10 and 11, for instance, if a certain gene letter is A, and the prediction character c is A at the same, an XOR operation result (reversible computing result) of this bit is 00, otherwise the XOR operation result varies according to different input characters c; in decompressing, the XOR operation (reverse computing for the inverse function of the reversible function) is performed for the character coding and XOR operation result (reversible computing result) of the prediction character c again, namely, original gene characters can be restored. A, C, G and T gene letters are respectively coded as 00, 01, 10 and 11, which is a preferable streamlined coding way. Besides, other binary coding ways may be applied for reversible conversion between the gene characters, prediction characters and reversible computing results according to the needs. Without doubt, the bit subtraction may be applied for the reversible function in addition to the XOR computing. At this time, the bit addition is applied for the inverse function of the reversible function, and meanwhile, the gene letters, prediction characters and reversible computing results can be converted reversibly.

Compression in step A2) specifically refers to compression using a statistical model and entropy coding.

It should be noted that the aforesaid compression method is only an example applied by the gene sequencing data compression preprocessing method in this embodiment. As described above, reversible computing (equivalent to XOR or bit subtraction) is performed by virtue of the reversible function according to the prediction character c and an original character, that is, the correct prediction bits are changed as the same characters. Based on the basic principle of compression algorithm, the more the same characters are, the lower the implemented compression ratio will be. For this, the more accurate the prediction information of the gene sequencing data compression preprocessing method of this embodiment is, the lower the compression ratio of the genome data sample will be. Inspired by this, those skilled in the art should determine that the gene sequencing data compression preprocessing method of this embodiment is not limited to being applied to the special case of the aforesaid compression method.

Meanwhile, this embodiment further provides a gene sequencing data compression preprocessing system based on character prediction, comprising a computer system, wherein the computer system is programmed to perform the steps of the aforesaid gene sequencing data compression preprocessing method of this embodiment. It will not be repeated again. Meanwhile, this embodiment further provides a computer-readable medium, on which a computer program is stored, wherein the computer program allows the computer system to perform the steps of the aforesaid gene sequencing data compression preprocessing method of this embodiment. It will not be repeated again.

Embodiment 1.2

This embodiment is essentially the same as Embodiment 1.1, the main different point between which is different ways for constructing the prediction data model P1. In this embodiment, a mapping relation between any short string K-mer in the positive strand S1 and the negative strand S2 and a prediction character c of a corresponding adjacent bit thereof is not acquired by the statistics, while a training set is generated by the short strings K-mer corresponding to the tuples in a positive strand prediction set KP1 and a negative strand prediction set KP2 and base letters co of the corresponding adjacent bits in the positive strand S1 or the negative strand S2 thereof, a neural network model is trained by the training set, and the trained neural network model is taken as the prediction data model P1.

In this embodiment, step 2.3) comprises the following detailed steps:

S2.3.1) with respect to the positive strand short string set KS1, sequentially extracting the short string K-mer and constructing positive strand prediction set KP1, so that every element in the positive strand short string set KS1 has one corresponding tuple in the positive strand prediction set KP1, and the tuple at least contains three types of information: short string K-mer, mark d from the positive strand, and the base letter $c_0$ in the adjacent bit of the positive strand S1;

S2.3.2) with respect to the negative strand short string set KS2 sequence, extracting the short string K-mer and constructing negative strand prediction set KP2, so that every element in the negative strand short string set KS2 has one corresponding tuple in the negative strand prediction set KP2, and the tuple at least contains three types of information: short string K-mer, mark d from the negative strand, and the base letter $c_0$ in the adjacent bit of the negative strand S2;

S2.3.3) generating a training set by the short strings K-mer corresponding to the tuples in a positive strand prediction set KP1and a negative strand prediction set KP2 and a base letter co corresponding to the adjacent bit in the positive strand S1 or the negative strand S2 thereof, training a neural network model by the training set, and taking the trained neural network mode as the prediction data model P1 containing any short string K-mer in positive strand and negative strand of the reference genome and the prediction data model P1 of the prediction character c in the corresponding adjacent bit.

Correspondingly, when the prediction data model P1 obtained by the gene sequencing data compression preprocessing method of this embodiment is used for gene sequencing data compression, step A2.2.2) of obtaining the prediction character c corresponding to every tuple (k-mer, 0) in the positive strand prediction sequence KP1 by a mapping function of the prediction data model P1 specifically refers to inputting a neural network model of every tuple (k-mer, 0) in the positive strand prediction sequence KP1 to obtain the prediction character c corresponding to the tuple (k-mer, 0); step A2.2.4) of obtaining the prediction character c corresponding to every tuple (k-mer, 1) in the negative strand prediction sequence KP2 through the mapping function of the prediction data model P1 specifically refers to inputting every tuple (k-mer, 1) in the positive strand prediction sequence KP2 into the neural network model to obtain the prediction character c corresponding to the tuple (k-mer, 1).

II. With Respect to Gene Sequencing Data Compression Method of the Present Invention Embodiment 2.1

Figure 2:
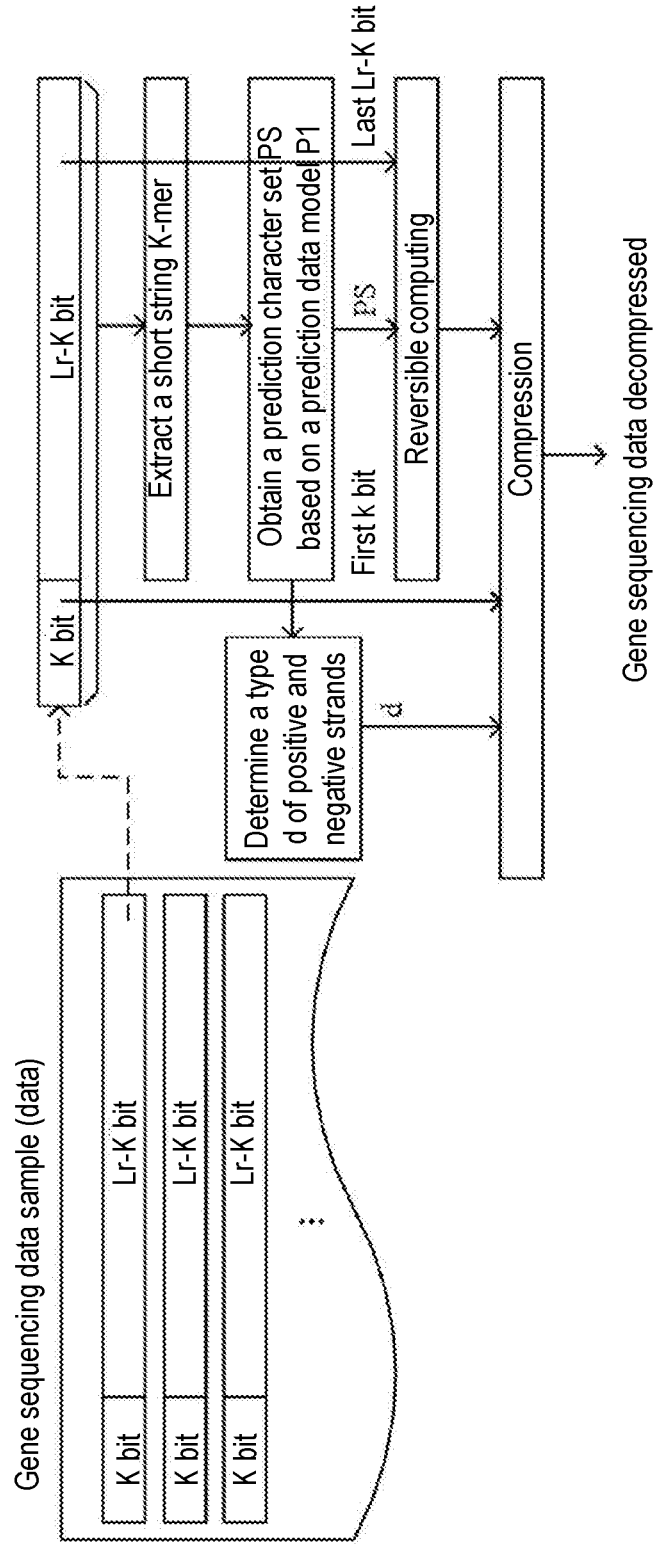
FIG. 2 is a basic flow diagram of the compression method in embodiment 2.1 of the present invention.

By referring to FIG. 2, the gene sequencing data compression method of this embodiment comprises the following implementation steps:

1) traversing a gene sequencing data sample (data) to obtain a read sequence R with a length of Lr bit;

2) with respect to every read sequence R, selecting the k bit original gene letter as the original gene character string $CS_0$, generating a character string in the k bit with fixed length based on the length of k bit as the sliding window sequence from the original gene character string $CS_0$, as short string K-mer, determining a type d of positive and negative strands of the read sequence R based on the short string K-mer, and obtaining a prediction character c in the adjacent bit corresponding to every short string K-mer through the preset prediction data model P1 to obtain a prediction character set PS with a length of Lr–k bit, wherein the prediction data model P1 contains any short string K-mer in the positive and negative strands of the reference genome and a prediction character c in corresponding adjacent bit; performing reversible computing by the reversible function after coding the Lr–k bit original gene letter and the prediction character set PS exclusive of k bit original gene letter in the read sequence R, wherein the output computing results coded by any pair of same characters are identical by virtue of the reversible function; compressing and outputting the type d of the positive and negative strands of the read sequence R, the original gene character string $CS_0$ and reversible computing result, as three data flows. In this embodiment, the type d of positive and negative strands is 0 or 1, 0 indicates the read sequence R from the positive strand, and 1 indicates the read sequence R from the negative strand.

It should be pointed out that, when the prediction character c in the adjacent bit is obtained, the definition of the adjacent bit is associated with the way of selecting an original gene character string $CS_0$, and the adjacent bit refers to a next bit if the original gene character string $CS_0$ is a first k bit of the read sequence R; the adjacent bit refers to the last bit if the original gene character string $CS_0$ is a last k bit of the read sequence; the adjacent bit comprises the last and next bits if the original gene character string $CS_0$ is the middle k bit of the read sequence R. By referring to FIG. 2, the adjacent bit in this embodiment specifically refers to the next bit, namely the first k bit original gene letter is selected when the original gene character string $CS_0$ is selected; the Lr–k bit original gene letter excluding the k bit original gene letter in the read sequence R specifically refers to the last Lr–k bit original gene letter in the read sequence R.

In this embodiment, step 2) comprises the following implementation steps:

2.1) traversing a read sequence R with a length of Lr from the gene sequencing data sample (data), with respect to the read sequence R, selecting k bit original gene letter as the original gene character string $CS_0$, generating fixed length substring based on the k bit length as the sliding window sequence from the original gene character string $CS_0$, as the short string K-mer, and obtaining the read sequence short string set KR;

2.2) generating fixed length substring as the short string K-mer according to the sequence, determining a type d of positive and negative strands of the read sequence R based on the short string K-mer, and obtaining a prediction character c in corresponding adjacent bit of every short string K-mer to obtain a prediction character set PS with a length of Lr–k bit through a preset prediction data model P1, P1, wherein the prediction data model P1 contains any short string K-mer in the positive and negative strands of the reference genome and a prediction character c thereof in the corresponding adjacent bit;

2.3) performing reversible computing by the reversible function after coding the Lr–k bit original gene letter and the prediction character set PS exclusive of k bit original gene letter in the read sequence R, wherein the output computing results coded by any pair of same characters are identical by virtue of the reversible function;

2.4) compressing and outputting the type d of the positive and negative strands of the read sequence R, the original gene character string $CS_0$ and reversible computing result, as three data flows;

2.5) judging whether the read sequence R in the gene sequencing data sample (data) is traversed, if not, jumping to step 2.1); otherwise ending and exiting.

It should be noted that the read length Lr of the read sequence R may be designated according to the needs, for example, a long enough read length Lr can be designated to designate a gene sequencing data sample (data) to one read sequence R in some extreme conditions.

In this embodiment, step 2.2) comprises the following detailed steps:

2.2.1) sequentially extracting a short string K-mer with respect to the read sequence short string set KR, constructing a positive strand prediction sequence KP1 based on the short string K-mer, wherein any short string K-mer in a read sequence short string set KR has a corresponding tuple (k-mer, 0) in the positive strand prediction sequence KP1, k-mer is the short string K-mer, and 0 indicates supposing the short string K-mer from the positive strand;

2.2.2) obtaining the prediction character c corresponding to every tuple (k-mer, 0) in the positive strand prediction sequence KP1 through the prediction data model P1, P1, so as to obtain a positive strand prediction character sequence PS1 formed by all prediction characters c; the prediction data model P1 contains any short string K-mer in the positive and negative strands of the reference genome and a prediction character c corresponding to the adjacent bit thereof;

2.2.3) sequentially extracting a short string K-mer with respect to the read sequence short string set KR, constructing a negative strand prediction sequence KP2 based on the short string K-mer, wherein any short string K-mer in the read sequence short string set KR has a corresponding tuple (k-mer, 1) in the negative strand prediction sequence KP2, k-mer is the short string K-mer, and 1 indicates supposing the short string K-mer from the negative strand;

2.2.4) obtaining the prediction character c corresponding to the adjacent bit through the prediction data model P1 with respect to every tuple (k-mer, 1) in the negative strand prediction sequence KP2, and obtaining the negative strand prediction character sequence PS2 formed by all prediction characters c;

2.2.5) calculating an editing distance L1 between the positive strand prediction character sequence PS1 and Lr−k bit original gene letter exclusive of k bit original gene letter in the read sequence R, calculating an editing distance L2 between the negative strand prediction character sequence PS2 and the Lr−k bit original gene letter exclusive of k bit original gene letter in the read sequence R;

2.2.6) judging whether the editing distance L1 is less than L2, if yes, determining the type d of the positive and negative strands of the read sequence R to be a positive strand, and the positive strand prediction character sequence PS1 to be the prediction character set PS in Lr−k bit; otherwise, determining the type d of the positive and negative strands of the read sequence R to be negative strand, and the negative strand prediction character sequence PS2 to be the prediction character set PS in Lr−k bit.

If the k bit original gene letter is selected as the first k bit of the read sequence R, the prediction character set PS is substantially the prediction character set corresponding to the last Lr−k bit of the read sequence R; if the k bit original gene letter is the last k bit of the read sequence R, the prediction character set PS is substantially the prediction character set corresponding to the first Lr−k bit of the read sequence; if the k bit original gene letter is selected as the middle k bit of the read sequence R, the prediction character set PS substantially comprises two parts of prediction character sets, the total length of which is Lr−k bit, corresponding to the Lr−k original gene letter excluding the k bit original gene letter in the read sequence R.

In this embodiment, the prediction data model P1 is a gene character string with a length of L. Step 2.2.2) of obtaining the prediction character c in the adjacent bit thereof corresponding to every tuple (k-mer, 0) in the positive strand prediction sequence KP1 through the prediction data model P1 comprises the following detailed steps:

2.2.2.1) mapping every tuple (k-mer, 0) in the positive strand prediction sequence KP1 to a certain line of an integer set [0, L] using a mapping function corresponding to the prediction data model P1, P1, wherein L is a supremum of the integer set which is as long as the prediction data model P1, and 0 is an infimum of the integer set; generating a one-dimensional (1D) table T1 with a length of (Lr−k+1) according to a mapping result, wherein the i(th) element T1[i] in the 1D table T1 is respectively and sequentially stored and mapped to a value of the mapping function corresponding to the tuple (k-mer, 0) in the i(th) line of the integer set, i∈[0, Lr−k];

2.2.2.2) obtaining a prediction character c corresponding to the adjacent bit from the prediction data model P1 according to the value of the mapping function corresponding to each tuple of 1D table T1, and generating 1D character sequence PS1, so that the i(th) PS1[i] value of the 1D character sequence PS 1 is equal to the i(th) character P1[T1[i]] in the prediction data model P1, and the i(th) character P1[T1[i]] in the prediction data model P1 is the corresponding character c with the mapping function value of PS1[i] corresponding to the tuple (k-mer, 0), wherein i∈[0, Lr−k], Lr is a read length of the read sequence R, and k is the length of the short string K-mer.

In this embodiment, step 2.2.4) of obtaining the prediction character c in the adjacent bit thereof corresponding to every tuple (k-mer, 1) in the negative strand prediction sequence KP2 through the prediction data model P1 comprises the following detailed steps:

2.2.4.1) mapping every tuple (k-mer, 1) in the negative strand prediction sequence KP2 to a certain line of an integer set [0, L] using the mapping function corresponding to the prediction data model P1, P1, wherein L is a supremum of the integer set which is as long as the prediction data model P1, P1, and 0 is an infimum of the integer set; generating a 1D table T2 with a length of (Lr−k+1) according to a mapping result, wherein the i(th) element T2[i] in the 1D table T2 is respectively and sequentially stored and mapped to a value of the mapping function corresponding to the tuple (k-mer, 1) in the i(th) line of the integer set, i∈[0, Lr−k];

2.2.4.2) obtaining the prediction character c corresponding to the adjacent bit thereof from the prediction data model P1 thereof according to the value of the mapping function corresponding to each tuple (k-mer, 1) in the 1D table T2, and generating the 1D character sequence PS2, so that the i(th) PS2[i] value of the 1D character sequence PS2 is equal to an i(th) character P1[T2[i]] in the prediction data model P1, P1, wherein the i(th) character P1[T2[i]] in the prediction data model P1 is the corresponding prediction character c with a mapping function value of PS2[i] corresponding to the tuple (k-mer, 0), i∈[0, Lr−k], Lr is a read length of the read sequence R, and k is the length of the short string K-mer.

It should be noted that, the length L of the prediction data model P1 involves the compression performance and compression ratio; if the length L of the prediction data model P1 is greater, the opportunity of generating a conflict is smaller and the prediction accuracy will be higher when the sub-tuple (k-mer, d) of every tuple (k-mer, d, $c_0$) withdrawn is mapped to a certain line in an integer set [0, L] to generate a 2D statistical table F with L lines and 4 columns, however, this may result in more computing consumption resources; on the contrary, if the length L of the prediction data model P1 is smaller, the opportunity of generating a conflict is greater, the prediction accuracy will be lower, and the computing consumption resources are fewer when the sub-tuple (k-mer, d) of every tuple (k-mer, d, $c_0$) withdrawn is mapped to a certain line in an integer set [0, L] to generate a 2D statistical table F with L lines and 4 columns.

In this embodiment, an XOR function is specifically applied for the reversible function in step 2). In this embodiment, A, C, G and T gene letters are respectively coded as 00, 01, 10 and 11, for instance, if a certain gene letter is A, and a prediction character c is A at the same, an XOR operation result (reversible computing result) of this bit is 00, otherwise the XOR operation result varies according to different input characters c; in decompressing, the XOR operation (reverse computing for the inverse function of the reversible function) is performed for the character coding and XOR computing results (reversible computing result) of the prediction character c again, namely, original gene characters can be restored. A, C, G and T gene letters are respectively coded as 00, 01, 10 and 11, which is a preferable streamlined coding way. Besides, other binary coding ways may be applied for reversible conversion between the gene characters, prediction characters and reversible computing results according to the needs. Without doubt, the bit subtraction function may be applied for the reversible function in addition to the XOR computing. At this time, the bit addition is applied for the inverse function of the reversible function, and meanwhile, the gene letters, prediction characters and reversible computing results can be converted reversibly.

In this embodiment, compression in step 2) specifically refers to compression using a statistical model and entropy coding.

In this embodiment, the detailed steps of generating the prediction data model P1 in step 1) are as follows:

A1) obtaining a reference genome data ($data_{ref}$) to be processed (the reference genome data ($data_{ref}$) is a gene sequence obtained by sequencing a certain specific individual complete or partial reference genome of one or a plurality of species);

A2) obtaining a mapping relation between any fixed length substring as the short string K-mer in the reference genome data ($data_{ref}$) and the prediction character c thereof, so as to obtain a prediction data model P1 including any short string K-mer in the positive and negative strands of the reference genome and the prediction character c in the corresponding adjacent bit thereof. The length k of the short string K-mer is generally valued as a specific value between 16 and 32.

Step A2) comprises the following implementation steps:

A2.1) extracting the fixed length substring in the positive strand S1 of the reference genome data ($data_{ref}$) as the short string K-mer to construct a positive strand short string set KS1 according to the designated space sequence, wherein the positive strand S1 is the reference genome data ($data_{ref}$) of the original sequence;

A2.2) extracting the fixed length substring in the negative strand S2 of the reference genome data ($data_{ref}$) as the short string K-mer to construct a negative strand short string set KS2 according to the designated space sequence, wherein the negative strand S2 is the negative sequence complementary gene sequence of the reference genome data ($data_{ref}$), and between the negative sequence complementary gene sequence and the reference genome data ($data_{ref}$), the bases A and T are interchanged, and the bases C and G are interchanged;

A2.3) generating the prediction data model P1 corresponding to the reference genome data ($data_{ref}$) according to the positive strand short string set KS1 and negative strand short string set KS2, wherein the prediction data model P1 contains the mapping relation between any short string K-mer in positive strand S1 and negative strand S2 and the prediction character c in the most possible next bit obtained from statistics.

Step A2.3) comprises the following detailed steps:

A2.3.1) with respect to the positive strand short string set KS1, sequentially extracting the short string K-mer and constructing the positive strand prediction set KP1, wherein every element in the positive strand short string set KS1 has one corresponding tuple in the positive strand prediction set KP1, and the tuple at least contains three types of information: short string K-mer, mark d from the positive strand, and the next base letter $c_0$ in the positive strand S1;

A2.3.2) with respect to the negative strand short string set KS2, sequentially extracting the short string K-mer and constructing negative strand prediction set KP2, wherein every element in the negative strand short string set KS2 has one corresponding tuple in the negative strand prediction set KP2, and the tuple at least contains three types of information: short string K-mer, mark d from the negative strand, and the next base letter $c_0$ of the element in the negative strand S2;

A2.3.3) mapping the tuples in the positive strand prediction set KP1 and negative strand prediction set KP2 to the base letters A, C, G and T, counting any short string K-mer in the positive strand S1 and negative strand S2 and the base letters in the most possible adjacent bits obtained from statistics, obtaining the prediction data model P1 containing the mapping relation between any short string K-mer in positive strand S1 and negative strand S2 and the prediction character c in the most possible next bit obtained from statistics.

Step A2.3.3) comprises the following detailed steps:

A2.3.3.1) taking out every tuple (k-mer, d, $c_0$) one by one from the positive strand prediction set KP1and the negative strand prediction set KP2, wherein k-mer is the short string K-mer corresponding to the tuple, d is the type of positive and negative strands, d=0 indicates the positive strand, d=1 indicates the positive strand, $c_0$ is the next base letter corresponding to the short string K-mer of the corresponding tuple in the positive strand S1 or the negative strand S2;

A2.3.3.2) using a preset mapping function to map a sub-tuple (k-mer, d) of every tuple (k-mer, d, $c_0$) taken out to a certain line of the integer set [0, L] so as to generate a 2D statistical table F containing L lines and 4 columns, and determining a corresponding column of a hit line of the corresponding next base letter $c_0$ in the positive strand S1 or the negative strand S2 by virtue of the short string K-mer corresponding to the tuple in the tuple (k-mer, d, $c_0$), wherein L is a supremum of the integer set, and 0 is an infimum of the integer set; the number of base letters A, C, G and T corresponding to every value in the integer set and 4 lines of corresponding base letters A, C, G and T in the 2D statistical table F are counted; an element $F_{i,c}$ in the 2D statistical table F stores the number of the base letters A, C, G and T corresponding to the sub-tuple (k-mer, d) with a value of i, in which a subscript i∈[0, L], c∈{A, C, G and T};

A2.3.3.3) traversing the 2D statistical table F from lines 0 to L, constructing the base letters corresponding to the element $F_{i,c}$ with the maximum value in every line to be a 1D character sequence as a prediction data model P1, P1, wherein the length of the prediction data model P1 is L, L is the supremum of the integer set, the i(th) character P1[i] of the prediction data model P1 indicates the prediction character c of the short string K-mer corresponding to the tuple in the i(th) line of the integer set.

Step A 2.3.3.2) of counting the number of A, C, G and T corresponding to every value in the integer set specifically refers to: when the sub-tuple (k-mer, d) of every tuple (k-mer, d, $c_0$) taken out is mapped to an integer set [0, L], with respect to four elements $F_{i,c}$ in every line of the 2D statistical table F, four count values $F_{i,A}$, $F_{i,C}$, $F_{i,G}$, $F_{i,T}$ are set, respectively; if the next base letter $c_0$ of the short string K-mer corresponding to the tuple in the i(th) line of the integer set in the corresponding positive strand S1 or negative strand S2 is hit as $F_{i,A}$, in the i(th) line is plus 1; if the next base letter $c_0$ of the short string K-mer corresponding to the tuple in the i(th) line of the integer set in corresponding positive strand S1 or negative strand S2 is hit as C, $F_{i,C}$ in the i(th) line is plus 1; if the next base letter $c_0$ of the short string K-mer corresponding to the tuple in the i(th) line of the integer set in corresponding positive strand S1 or negative strand S2 is hit as G, $F_{i,G}$ in the i(th) line is plus 1; the next base letter $c_0$ of the short string K-mer corresponding to the tuple in the i(th) line of the integer set in corresponding positive strand S1 or negative strand S2 is hit as T, $F_{i,T}$ in the i(th) line is plus 1; finally the numbers $F_{i,A}$, $F_{i,C}$, $F_{i,G}$, $F_{i,T}$ of A, C, G, T corresponding to every value in the integer set are obtained.

To sum up, the gene sequencing data compression method of this embodiment can conform to the requirements of lossless gene sequencing data compression, low compression ratio, short compression time and stable performance, and is capable of extremely alleviating the challenges for storage, management, retrieval and transmission technologies and costs encountered by the gene testing data.

This embodiment further provides a gene sequencing data compression system, comprising a computer system, wherein the computer system is programmed to perform the steps of the aforesaid gene sequencing data compression method of this embodiment. It will not be repeated again. This embodiment further provides a computer-readable medium, on which a computer program is stored, wherein the computer program allows the computer to perform the steps of the aforesaid gene sequencing data compression method of this embodiment. It will not be repeated again.

Embodiment 2.2

This embodiment is essentially the same as Embodiment 2.1, the main distinguishing point between which is different prediction data models P1 in step 1).

In this embodiment, the prediction data model P1 is the neural network model which is trained in advance based on the short string K-mer in the reference genome and the corresponding base letter $c_0$ in the adjacent bit thereof; step 2.2.2) of obtaining the prediction character c in the adjacent bit thereof corresponding to every tuple (k-mer, 0) in the positive strand prediction sequence KPI through the mapping function of the prediction data model P1 specifically refers to inputting every tuple (k-mer, 0) in the positive strand prediction sequence KP1 into the neural network model to obtain the prediction character c corresponding to the tuple (k-mer, 0); step 2.2.4) of obtaining the prediction character c in the adjacent bit thereof corresponding to every tuple (k-mer, 1) in the negative strand prediction sequence KP2 through the prediction data model P1 specifically refers to inputting every tuple (k-mer, 1) in the negative strand prediction sequence KP2 into the neural network model to obtain the prediction character c corresponding to the tuple (k-mer, 1).

Correspondingly, in step A2.3) of Embodiment 2.1, the detailed steps of generating the prediction data model P1 in this embodiment are as follows:

B2.3.1) with respect to the positive strand short string set KS1, sequentially extracting the short string K-mer and constructing the positive strand prediction set KP1, so that every element in the positive strand short string set KS1 has one corresponding tuple in the positive strand prediction set KP1, wherein the tuple at least contains three types of information: short string K-mer, mark d from the positive strand, and the next base letter $c_0$ in the positive strand S1;

B2.3.2) with respect to the negative strand short string set KS2 sequence, extracting the short string K-mer and constructing negative strand prediction set KP2, so that every element in the negative strand short string set KS2 has one corresponding tuple in the negative strand prediction set KP2, and the tuple at least contains three types of information: short string K-mer, mark d from the negative strand, and the next base letter $c_0$ in the negative strand S2;

B2.3.3) generating a training set by the short strings K-mer corresponding to the tuples in a positive strand prediction set KP1 and a negative strand prediction set KP2 and a corresponding next base letter $c_0$ in the positive strand S1 or the negative strand S2 thereof, training the neural network model by the training set, and taking the trained neural network mode as the prediction data model P1.

III. With Respect to Gene Sequencing Data Decompression Method of the Present Invention Embodiment 3.1

Figure 3:
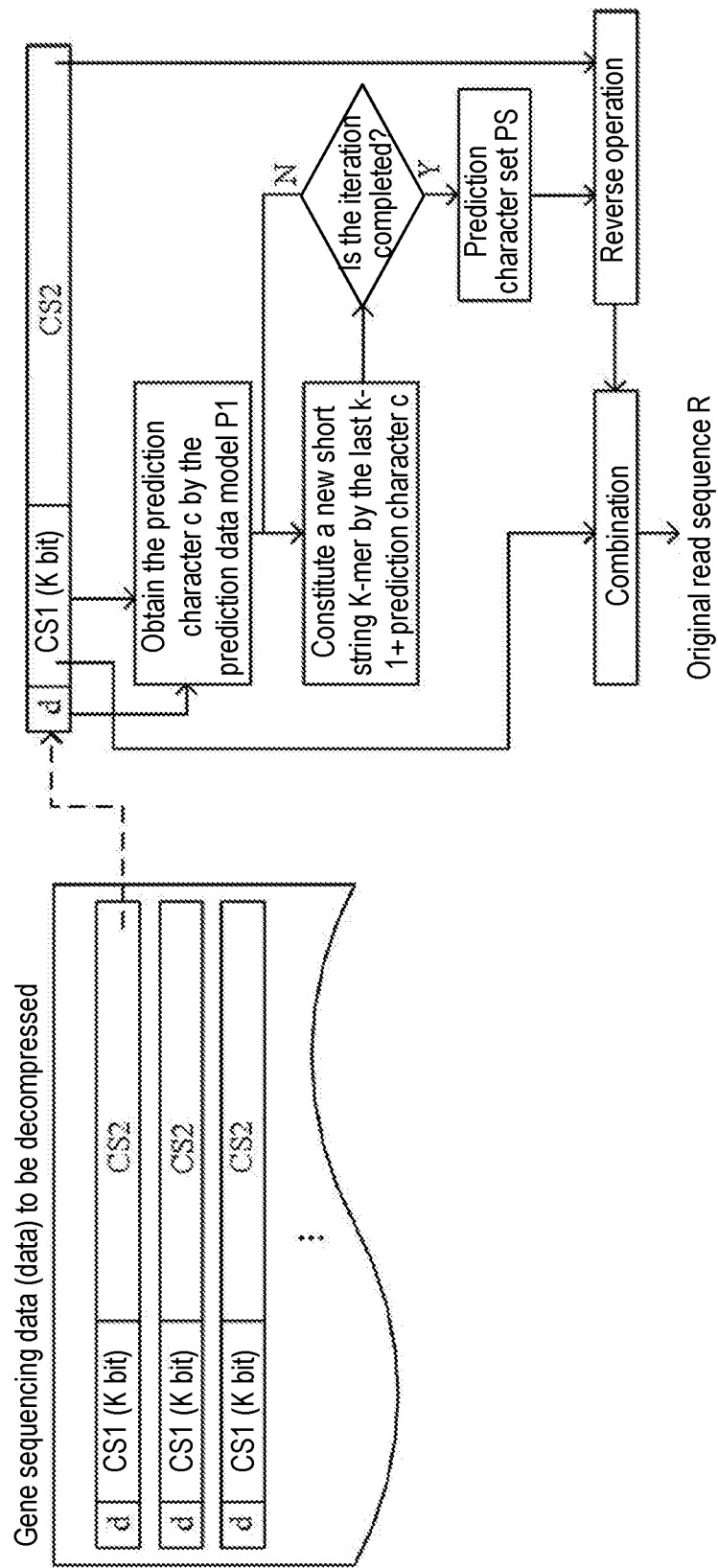
FIG. 3 is a basic flow diagram of the decompression method in embodiment 3.1 of the present invention.

By referring to FIG. 3, the gene sequencing data decompression method of this embodiment comprises the following implementation steps:

1) traversing gene sequencing data ($data_c$) to be decompressed to obtain a read sequence $R_c$ to be decompressed;

2) decompressing and reconstructing every read sequence $R_c$ to be decompressed to be the positive and negative strands type d, the original gene sequence CS1 in the k bit and the reversible computing result CS2 with the length of Lr−k bit; taking the original gene sequence CS1 in the k bit as the initial short string K-mer, and obtaining the corresponding prediction character c in the adjacent bit of the short string K-mer through the preset prediction data model P1, P1, wherein the prediction data model P1 contains any short string K-mer in the positive and negative strands of the reference genome and the corresponding prediction character c in the adjacent bit thereof; when one prediction character c is obtained, constituting a new short string K-mer by the prediction character c and the last k-1 bit of the short string K-mer, obtaining the new prediction character c by the preset prediction data model P1, P1, and eventually obtaining the prediction character set PS with a length of Lr−k bit constituted by all prediction characters c; performing the reverse computing for the coded reversible computing result CS2 and the prediction character set PS to obtain the decrypted result of the reversible computing result CS2 in the Lr−k bit by virtue of the inverse function of the reversible function; combining the decrypted results of the original gene sequence CS1 in the k bit and the reversible computing result CS2 to obtain the original read sequence R corresponding to the read sequence $R_c$ to be decompressed, and outputting the original read sequence R.

It should be noted that the definition of the adjacent bit is associated with the position definition of the original gene sequence CS1 in the k bit when the prediction character c in the adjacent bit is obtained; the adjacent bit is the next bit if the position of the original gene sequence CS1 in the k bit is defined to be the first k bit of the read sequence R; the adjacent bit is the last bit if the position of the original gene sequence CS1 in the k bit is defined to be the last k bit of the read sequence R; the adjacent bit comprises the last and next bits if the position of the original gene sequence CS1 in the k bit is defined to the middle k bit of the read sequence R. By referring to FIG. 3, the position of the original gene sequence CS1 in the k bit in this embodiment is defined as the first k bit of the read sequence R, and the adjacent bit specifically refers to the next bit. Correspondingly, the reversible computing result CS2 with a length of Lr–k bit is an encrypted content corresponding to the last Lr–k bit original gene letter in the CS2 read sequence R.

In this embodiment, the step 2) comprises the following detailed steps:

2.1) traversing gene sequencing data (data) to be decompressed to obtain the read sequence $R_c$ to be decompressed;

2.2) decompressing and reconstructing the read sequence $R_c$ to be decompressed to be the positive and negative strands type d, the original gene sequence CS1 in the k bit and the reversible computing result CS2 with the length of Lr–k bit, wherein the type d of the positive and negative strands is 0 or 1, 0 indicates the read sequence R from the positive strand, and 1 indicates the read sequence R from the negative strand;

2.3) taking the original gene sequence CS1 in the k bit as the initial short string K-mer, and obtaining the corresponding prediction character c in the adjacent bit of the short string K-mer through the preset prediction data model P1, P1, wherein the prediction data model P1 contains any short string K-mer in the positive and negative strands of the reference genome and the corresponding prediction character c in the adjacent bit thereof; when one prediction character c is obtained, forming a new short string K-mer constituted by new prediction character c and the last k-1 bit of the short string K-mer, obtaining the new prediction character c by the preset prediction data model P1, P1, and eventually obtaining the prediction character set PS with a length of Lr–k bit constituted by all prediction characters c;

2.4) performing the reverse computing for the coded reversible computing result CS2 and the prediction character set PS to obtain the decrypted result of the reversible computing result CS2 in the Lr–k bit by virtue of the inverse function of the reversible function;

2.5) combining the decrypted results of the original gene sequence CS1 in the k bit and the reversible computing result CS2 to obtain the original read sequence R corresponding to the read sequence $R_c$ to be decompressed, and outputting the original read sequence R;

2.6) judging whether the read sequence $R_c$ to be decompressed in the gene sequencing data sample (data$_c$) to be decompressed is traversed, if not, jumping to step 2.1); otherwise ending and exiting.

It should be noted that when the decrypted results of the original gene sequence CS1 in the k bit and the reversible computing result CS2 are combined in step 2.5), it is needed to keep an original sequence of combining the decrypted results of the original gene sequence CS1 in the k bit and the reversible computing result CS2 . If the position of the original gene sequence CS1 in the k bit is defined to be the first k bit of the read sequence R, the decrypted results of the original gene sequence CS1 in the k bit and the reversible computing result CS2 are combined in such a manner of the original gene sequence CS1 in the k bit before the reversible computing result CS2. If the position of the original gene sequence CS1 in the k bit is defined to be the last k bit of the read sequence R, the decrypted results of the original gene sequence CS1 in the k bit and the reversible computing result CS2 are combined in such a manner of the original gene sequence CS1 in the k bit behind the reversible computing result CS2. If the position of the original gene sequence CS1 in the k bit is defined to be the middle k bit of the read sequence R, the adjacent bit comprises the last bit and the next bit. At this time, the decrypted results of the reversible computing result CS2 also comprise a plurality of bits before the original gene sequence CS1 in the k bit and a plurality of bits behind the original gene sequence CS1 in the k bit. By this time, the plurality of bits before the original gene sequence CS1 in the k bit, the original gene sequence CS1 in the k bit and the plurality of bits behind original gene sequence CS1 in the k bit are combined.

In this embodiment, step 2.3) comprises the following detailed steps:

2.3.1) creating a window variable CS and a prediction character set PS corresponding to the short string K-mer, setting the initial value of the window variable CS as the original gene sequence CS1 in the k bit, creating an iteration variable j and setting the initial value as 0;

2.3.2) constructing the window variable CS, the type d of positive and negative strands of the read sequence Re to be decompressed into a tuple (CS, d), mapping the tuple (CS, d) into an integer set [0, 1] by the mapping function, wherein L is the supremum of the integer set and equal to the length of the prediction data model P1; 0 is the infimum of the integer set, and the prediction data model P1 contains any short string K-mer in the positive and negative strands of the reference genome and a prediction character c thereof corresponding to the adjacent bit;

2.3.3) querying the i(th) P1[i] in the prediction data model P1 with the function value obtained from the mapping function, as the prediction character c corresponding to the adjacent bit of the window variable CS, wherein i∈[0, L]; assigning the prediction character c to the j(th) bit in the prediction character set PS, wherein j∈[0, Lr-k], and Lr–k is the length of reversible computing result CS2.

2.3.4) after combining the last k-1 bit of the window variable CS and the prediction character c obtained currently, assigning to the window variable CS, and adding 1 to the iteration variable j;

2.3.5) judging whether the iteration variable j is greater than the length (Lr–k) of the reversible computing result CS2, if yes, jumping to the next step, otherwise, jumping to step 2.3.2);

2.3.6) outputting the prediction character set PS with the length of (Lr–k).

In this embodiment, the reversible function in step 2.4) specifically refers to the XOR function, and the inverse function of the XOR operation is the XOR function. In this embodiment, A, C, G and T gene letters are respectively coded as 00, 01, 10 and 11, for instance, if a certain gene letter is A, and the prediction character c is A at the same, the XOR operation result (reversible computing result) of this bit is 00, otherwise the XOR operation result varies according to different input characters c; in decompressing, the XOR operation (reverse operation for the inverse function of the reversible function) is performed for the character coding and XOR operation result (reversible computing result) of the prediction character c again, namely, original gene characters can be restored. A, C, G and T gene letters are respectively coded as 00, 01, 10 and 11, which is a preferable streamlined coding way. Besides, other binary coding ways may be applied for reversible conversion between the gene characters, prediction characters and reversible computing results according to the needs. Without doubt, the bit subtraction function may be applied for the reversible function in step 2.4) in addition to the XOR computing. At this time, the bit addition function is applied for the inverse function of the reversible function, and meanwhile, the gene letters, prediction characters and reversible computing results can be converted reversibly.

In this embodiment, decompression and reconstruction in step 2) specifically refer to decompression and reconstruction using inverse algorithms of a statistical model and entropy coding.

In this embodiment, the detailed steps of generating the prediction data model P1 in step 1) are as follows:

A1) obtaining a reference genome data (data$_{ref}$) to be processed (the reference genome data (data$_{ref}$) is a gene sequence obtained by sequencing a certain specific individual complete or partial reference genome of one or a plurality of species);

A2) obtaining a mapping relation between any fixed length substring as the short string K-mer in the reference genome data (data$_{ref}$) and the prediction character c thereof, so as to obtain a prediction data model P1 including any short string K-mer in the positive and negative strands of the reference genome and the prediction character c of the corresponding adjacent bit thereof. The length k of the short string K-mer is generally valued as a specific value between 16 and 32.

Step A2) comprises the following implementation steps:

A2.1) extracting the fixed length substring in the positive strand S1 of the reference genome data (data$_{ref}$) as the short string K-mer to construct a positive strand short string set KS1 according to the designated space sequence, wherein the positive strand S1 is the reference genome data (data$_{ref}$) of the original sequence;

A2.2) extracting the fixed length substring in the negative strand S2 of the reference genome data (data$_{ref}$) as the short string K-mer to construct a negative strand short string set KS2 according to the designated space sequence, wherein the negative strand S2 is the negative sequence complementary gene sequence of the reference genome data (data$_{ref}$), and between the negative sequence complementary gene sequence and the reference genome data (data$_{ref}$), the bases A and T are interchanged, and the bases C and G are interchanged;

A2.3) generating the prediction data model P1 corresponding to the reference genome data (data$_{ref}$) according to the positive strand short string set KS1 and negative strand short string set KS2, wherein the prediction data model P1 contains the mapping relation between any short string K-mer in positive strand S1 and negative strand S2 and the prediction character c in the most possible next bit obtained from statistics.

Step A2.3) comprises the following detailed steps:

A2.3.1) with respect to the positive strand short string set KS1, sequentially extracting the short string K-mer and constructing the positive strand prediction set KP1, wherein every element in the positive strand short string set KS1 has one corresponding tuple in the positive strand prediction set KP1, and the tuple at least contains three types of information: short string K-mer, mark d from the positive strand, and the next base letter $c_0$ in the positive strand S1;

A2.3.2) with respect to the negative strand short string set KS2, sequentially extracting the short string K-mer and constructing negative strand prediction set KP2, wherein every element in the negative strand short string set KS2 has one corresponding tuple in the negative strand prediction set KP2, and the tuple at least contains three types of information: short string K-mer, mark d from the negative strand, and the next base letter $c_0$ of the element in the negative strand S2;

A2.3.3) mapping the tuples in the positive strand prediction set KP1 and negative strand prediction set KP2 to the base letters A, C, G and T, counting any short string K-mer in the positive strand S1 and negative strand S2 and the base letters in the most possible next bits obtained from statistics, and obtaining the prediction data model P1 containing the mapping relation between any short string K-mer in positive strand S1 and negative strand S2 and the prediction character c in the most possible next bit obtained from statistics.

Step A2.3.3) comprises the following detailed steps:

A2.3.3.1) taking out every tuple (k-mer, d, $c_0$) one by one from the positive strand prediction set KP1 and the negative strand prediction set KP2, wherein k-mer is the short string K-mer corresponding to the tuple, d is the type of positive and negative strands, d=0 indicates the positive strand, d=1 indicates the positive strand, $c_0$ is the base letter in the adjacent bit corresponding to the short string K-mer of the corresponding tuple in the positive strand S1 or the negative strand S2;

A2.3.3.2) using a preset mapping function to map a sub-tuple (k-mer, d) of every tuple (k-mer, d, $c_0$) taken out to a certain line of the integer set in a range of [0, L] so as to generate a 2D statistical table F containing L lines and 4 columns, and determining a corresponding column of a hit line of a corresponding base letter $c_0$ in the corresponding adjacent bit of the positive strand S1 or the negative strand S2 by virtue of the short string K-mer corresponding to the tuple in the tuple (k-mer, d, $c_0$), wherein L is a supremum of the integer set, and 0 is an infimum of the integer set;

counting the number of base letters A, C, G and T corresponding to every value in the integer set and 4 lines of corresponding base letters A, C, G and T in the 2D statistical table F, wherein an element $F_{i,c}$ in the 2D statistical table F stores the number of the base letters A, C, G and T corresponding to the sub-tuple (k-mer, d) with a value of i, in which a subscript i∈[0, L], c∈{A, C, G and T};

A2.3.3.3) traversing the 2D statistical table F from lines 0 to L, constructing the base letters corresponding to the element $F_{i,c}$ with the maximum value in every line to be a 1D character sequence as a prediction data model P1, P1, wherein the length of the prediction data model P1 is L, L is the supremum of the integer set, the i(th) character P1[i] of the prediction data model P1 indicates the prediction character c of the short string K-mer corresponding to the tuple in the i(th) line of the integer set.

Step A2.3.3.2) of counting the number of A, C, G and T corresponding to every value in the integer set specifically refers to: when the sub-tuple (k-mer, d) of every tuple (k-mer, d, $c_0$) taken out is mapped to an integer set [0, L], with respect to four elements $F_{i,c}$ in every line of the 2D statistical table, four count values $F_{i,A}$, $F_{i,C}$, $F_{i,G}$ and $F_{i,T}$ are set, respectively; if the base letter $c_0$ of the short string K-mer corresponding to the tuple in the i(th) line of the integer set in corresponding adjacent bit of the positive strand S1 or negative strand S2 is hit as A, $F_{i,A}$ in the i(th) line is plus 1; if the base letter $c_0$ of the short string K-mer corresponding to the tuple in the i(th) line of the integer set in corresponding adjacent bit of the positive strand S1 or negative strand S2 is hit as C, $F_{i,C}$ in the i(th) line is plus 1; if the base letter $c_0$ of the short string K-mer corresponding to the tuple in the i(th) line of the integer set in corresponding adjacent bit of the positive strand S1 or negative strand S2 is hit as G, $F_{i,G}$ in the i(th) line is plus 1; the base letter $c_0$ of the short string K-mer corresponding to the tuple in the i(th) line of the integer set in corresponding adjacent bit of the positive strand S1 or negative strand S2 is hit as T, $F_{i,T}$ in the i(th) line is plus 1; finally the numbers $F_{i,A}$, $F_{i,C}$, $F_{i,G}$, $F_{i,T}$ of A, C, G, T corresponding to every value in the integer set are obtained.

This embodiment further provides a gene sequencing data decompression system, comprising a computer system, wherein the computer system is programmed to perform the steps of the aforesaid gene sequencing data decompression method of this embodiment. Besides, this embodiment further provides a computer-readable medium, on which a computer program is stored, wherein the computer program allows the computer to perform the steps of the aforesaid gene sequencing data decompression method of this embodiment.

Embodiment 3.2

This embodiment is essentially the same as Embodiment 3.1, the main distinguishing point between which is different prediction data models P1 in step 1). In this embodiment, the prediction data model P1 is the neural network model trained based on the short string K-mer in the reference genome and the corresponding base letter $c_0$ in the adjacent bit thereof. Correspondingly, step 2.3) comprises the following detailed steps:

S2.3.1) creating a window variable CS and a prediction character set PS corresponding to the short string K-mer, setting the initial value of the window variable CS as the original gene sequence CS1 in the k bit, creating an iteration variable j and setting the initial value as 0;

S2.3.2) inputting the window variable CS to the prediction data model P1 to obtain the prediction character c of the short string K-mer corresponding to the adjacent bit in the positive strand and negative strand of the reference genome, wherein the prediction data model P1 is the neural network model which is trained in advance based on the short string K-mer in the reference genome and the base element $c_0$ corresponding to the adjacent bit thereof;

S2.3.3) assigning the prediction character c to the j(th) bit in the prediction character set PS, wherein $j \in [0, Lr-k]$, and Lr-k is the length of reversible computing result CS2.

S2.3.4) after combining the last k-1 bit of the window variable CS and the prediction character c obtained currently, assigning to the window variable CS, and adding 1 to the iteration variable j;

S2.3.5) judging whether the iteration variable j is greater than the length (Lr-k) of the reversible computing result CS2, if yes, jumping to the next step, otherwise, jumping to step 2.3.2);

S2.3.6) outputting the prediction character set PS with the length of (Lr-k).

Correspondingly, in step A2.3) of Embodiment 3.1, the detailed steps of generating the prediction data model P1 in this embodiment are as follows:

B2.3.1) with respect to the positive strand short string set KS1, sequentially extracting the short string K-mer and constructing the positive strand prediction set KP1, so that every element in the positive strand short string set KS1 has one corresponding tuple in the positive strand prediction set KP1, wherein the tuple at least contains three types of information: short string K-mer, mark d from the positive strand, and the next base letter $c_0$ in the positive strand S1;

B2.3.2) with respect to the negative strand short string set KS2 sequence, extracting the short string K-mer and constructing negative strand prediction set KP2, so that every element in the negative strand short string set KS2 has one corresponding tuple in the negative strand prediction set KP2, and the tuple at least contains three types of information: short string K-mer, mark d from the negative strand, and the next base letter $c_0$ in the negative strand S2;

B2.3.3) generating a training set by the short strings K-mer corresponding to the tuples in a positive strand prediction set KP1and a negative strand prediction set KP2 and a corresponding base letter $c_0$ in the adjacent bit of the positive strand S1 or the negative strand S2 thereof, training a neural network model by the training set, and taking the trained neural network mode as the prediction data model P1.

The above are only preferred embodiments of the present invention, and the protection scope of the present invention is not limited to the embodiment mentioned above. The technical solutions under the ideas of the present invention fall into the protection scope of the present invention. It should be pointed out that, for an ordinary person skilled in the art, some improvements and modifications without departing from the principle of the present invention shall be deemed as the protection scope of the present invention.

What is claimed is:

1. A gene sequencing data compression preprocessing method, comprising the following implementation steps:
    1) obtaining reference genome data $data_{ref}$;
    2) obtaining a mapping relation between any fixed length substring as the short string K-mer in the reference genome data $data_{ref}$ and the prediction character c thereof, so as to obtain a prediction data model P1 including any short string K-mer in the positive and negative strands of the reference genome and the prediction character c at the corresponding adjacent bit thereof.

2. The gene sequencing data compression preprocessing method as recited in claim 1, wherein the step 2) comprises the following implementation steps:
    2.1) sequentially extracting a fixed length substring in a positive strand S1 of the reference genome data $data_{ref}$ as the short string K-mer to construct a positive strand short string set KS1 according to the designated space, wherein the positive strand S1 is the reference genome data $data_{ref}$ of the original sequence;
    2.2) sequentially extracting a fixed length substring in a negative strand S2 of the reference genome data $data_{ref}$ as the short string K-mer to construct a negative strand short string set KS2 according to the designated space, wherein the negative strand S2 is a negative sequence complementary gene sequence of the reference genome data $data_{ref}$;
    and between the negative sequence complementary gene sequence and the reference genome data $data_{ref}$, the bases A and T are interchanged, and the bases C and G are interchanged;
    2.3) generating a prediction data model P1 corresponding to the reference genome data $data_{ref}$ according to the positive strand short string set KS1 and negative strand short string set KS2, wherein the prediction data model P1 contains the mapping relation between any short string K-mer in positive strand S1 and negative strand S2 and the prediction character c in the most possible adjacent bit obtained from statistics.

3. The gene sequencing data compression preprocessing method as recited in claim 2, wherein the step 2.3) comprises the following detailed steps:
    2.3.1) with respect to the positive strand short string set KS1, sequentially extracting the short string K-mer and constructing a positive strand prediction set KP1, wherein every element in the positive strand short string set KS1 has one corresponding tuple in the positive strand prediction set KP1, and the tuple at least contains three types of information: short string K-mer, mark d from the positive strand, and the base letter $c_0$ in the adjacent bit of the positive strand S1;
    2.3.2) with respect to the negative strand short string set KS2, sequentially extracting the short string K-mer and constructing a negative strand prediction set KP2, wherein every element in the negative strand short string set KS2 has one corresponding tuple in the negative strand prediction set KP2, and the tuple at least contains three types of information: short string K-mer, mark d from the negative strand, and the base letter $c_0$ of the element in the adjacent bit of the negative strand S2;

2.3.3) mapping the tuples in the positive strand prediction set KP1 and negative strand prediction set KP2 to the base letters A, C, G, T, counting any short string K-mer in the positive strand S1 and negative strand S2 and the base letters in the most possible adjacent bits obtained from statistics, obtaining the prediction data model P1 containing any short string K-mer in positive strand and negative strand of the reference genome and the prediction data model P1 of the prediction character c in the corresponding adjacent bit.

4. The gene sequencing data compression preprocessing method as recited in claim 3, wherein the step 2.3.3) comprises the following detailed steps:

2.3.3.1) taking out every tuple (k-mer, d, $c_0$) one by one from the positive strand prediction set KP1 and the negative strand prediction set KP2, wherein k-mer is a short string K-mer corresponding to the tuple, d is the type of positive and negative strands, d=0 indicates the positive strand, d=1 indicates the positive strand, $c_0$ is the base letter of the adjacent bit corresponding to the short string K-mer of the corresponding tuple in the positive strand S1 or the negative strand S2;

2.3.3.2) using a preset mapping function to map a sub-tuple (k-mer, d) of every tuple (k-mer, d, $c_0$) taken out to a certain line of the integer set in a range of [0, L] so as to generate a 2D statistical table F containing L lines and 4 columns, and determining a corresponding line of a hit line of a corresponding base letter $c_0$ of the corresponding adjacent bit in the positive strand S1 or the negative strand S2 by virtue of the short string K-mer corresponding to the tuple in the tuple (k-mer, d, $c_0$), wherein L is a supremum of the integer set, and 0 is an infimum of the integer set; the number of base letters A, C, G, T corresponding to every value in the integer set and 4 columns of corresponding base letters A, C, G and T in the 2D statistical table F are counted; an element $F_{i,c}$ in the 2D statistical table F stores the number of the base letters A, C, G, T corresponding to the sub-tuple (k-mer, d) with a value of i, in which a subscript i∈[0, L], c∈{A, C, G and T};

2.3.3.3) traversing the 2D statistical table F from lines 0 to L, constructing the base letters corresponding to the element $F_{i,c}$, with the maximum value in every line to be a 1D character sequence as a prediction data model P1 containing any short string K-mer in the positive strand and negative strand of the reference genome and the prediction character c of the corresponding adjacent bit, wherein the length of the prediction data model P1 is L, L is the supremum of the integer set, the i(th) character P1[i] of the prediction data model P1 indicates the prediction character c of the short string K-mer corresponding to the tuple in the i(th) line of the integer set.

5. The gene sequencing data compression preprocessing method as recited in claim 4, wherein the step 2.3.3.2) of counting the number of A, C, G, T corresponding to every value in the integer set specifically refers to: when the sub-tuple (k-mer, d) of every tuple (k-mer, d, $c_0$) withdrawn is mapped to an integer set [0, L], with respect to four elements $F_{i,c}$ in every line of the 2D statistical table, four count values $F_{i,A}$, $F_{i,C}$, $F_{i,G}$, $F_{i,T}$ are set, respectively;

if the base letter $c_0$ of the short string K-mer corresponding to the tuple in the i(th) line of the integer set in corresponding adjacent bit of the positive strand S1 or negative strand S2 is hit as A, $F_{i,A}$ in the i(th) line is plus 1;

if the base letter $c_0$ of the short string K-mer corresponding to the tuple in the i(th) line of the integer set in corresponding adjacent bit of the positive strand S1 or negative strand S2 is hit as C, $F_{i,C}$ in the i(th) line is plus 1;

if the base letter $c_0$ of the short string K-mer corresponding to the tuple in the i(th) line of the integer set in corresponding adjacent bit of the positive strand S1 or negative strand S2 is hit as G, $F_{i,G}$ in the i(th) line is plus 1;

if the base letter $c_0$ of the short string K-mer corresponding to the tuple in the i(th) line of the integer set in corresponding adjacent bit of the positive strand S1 or negative strand S2 is hit as T, $F_{i,T}$ in the i(th) line is plus 1;

finally the numbers $F_{i,A}$, $F_{i,C}$, $F_{i,T}$ of A, C, G, T corresponding to every value in the integer set are obtained.

6. The gene sequencing data compression preprocessing method as recited in claim 2, wherein the step 2.3) comprises the following detailed steps:

S2.3.1) with respect to the positive strand short string set KS1, sequentially extracting the short string K-mer and constructing positive strand prediction set KP1, so that every element in the positive strand short string set KS1 has one corresponding tuple in the positive strand prediction set KP1, and the tuple at least contains three types of information: short string K-mer, mark d from the positive strand, and the base letter $c_0$ in the adjacent bit of the positive strand S1;

S2.3.2) with respect to the negative strand short string set KS2 sequence, extracting the short string K-mer and constructing negative strand prediction set KP2, so that every element in the negative strand short string set KS2 has one corresponding tuple in the negative strand prediction set KP2, and the tuple at least contains three types of information: short string K-mer, mark d from the negative strand, and the base letter $c_0$ in the adjacent bit of the negative strand S2;

S2.3.3) generating a training set by the short strings K-mer corresponding to the tuples in a positive strand prediction set KP1 and a negative strand prediction set KP2 and a base letter $c_0$ corresponding to the adjacent bit in the positive strand S1 or the negative strand S2 thereof, training a neural network model by the training set, and taking the trained neural network mode as the prediction data model P1 containing any short string K-mer in positive strand and negative strand of the reference genome and the prediction data model P1 of the prediction character c in the corresponding adjacent bit.

7. A gene sequencing data compression preprocessing system based on character prediction, comprising a computer system, wherein the computer system is programmed to perform the steps of the gene sequencing data compression preprocessing method as recited in claim 1.

8. A non-transitory computer-readable medium, on which a computer program is stored, the computer program allows the computer system to perform the steps of the gene sequencing data compression preprocessing method as recited in claim 1.

9. A gene sequencing data compression method, comprising the following implementation steps:
1) traversing a gene sequencing data sample data to obtain a read sequence R with a length of Lr bit;
2) with respect to every read sequence R, selecting a original gene letter in k bit as an original gene character string $CS_0$, generating k bit character string with fixed length based on the length of k bit as a sliding window sequence from the original gene character string $CS_0$, as short string K-mer, determining a type d of positive and negative strands of the read sequence R based on the short string K-mer, and obtaining a prediction character c in the adjacent bit corresponding to every short string K-mer through the preset prediction data model P1 to obtain a prediction character set PS with a length of Lr−k bit, wherein the prediction data model P1 contains any short string K-mer in the positive and negative strands of the reference genome and a prediction character c in corresponding adjacent bit;
performing reversible computing by a reversible function after coding the Lr−k bit original gene letter and the prediction character set PS exclusive of k bit original gene letter in the read sequence R, wherein the output computing results coded by any pair of same characters are identical by virtue of the reversible function;
compressing and outputting the type d of the positive and negative strands of the read sequence R, k bit original gene letter and reversible computing result, as three data flows.

10. The gene sequencing data compression method as recited in claim 9, wherein the step 2) comprises the following implementation steps:
2.1) traversing a read sequence R with a length of Lr from the gene sequencing data sample data, with respect to the read sequence R, selecting k bit original gene letter as an original gene character string $CS_0$, generating fixed length substring based on the k bit length as the sliding window sequence from the original gene character string $CS_0$, as the short string K-mer, and obtaining the read sequence short string set KR;
2.2) generating fixed length substring as the short string K-mer according to the sequence, determining the type d of positive and negative strands of the read sequence R based on the short string K-mer, and obtaining a prediction character c in corresponding adjacent bit of every short string K-mer to obtain a prediction character set PS with a length of Lr−k bit through a preset prediction data model P1, P1, wherein the prediction data model P1 contains any short string K-mer in the positive and negative strands of the reference genome and a prediction character c thereof in the corresponding adjacent bit;
2.3) performing reversible computing by the reversible function after coding the Lr−k bit original gene letter and the prediction character set PS exclusive of k bit original gene letter in the read sequence R, wherein the output computing results coded by any pair of same characters are identical by virtue of the reversible function;
2.4) compressing and outputting the type d of the positive and negative strands of the read sequence R, the original gene character string $CS_0$ and reversible computing result, as three data flows;
2.5) judging whether the read sequence R in the gene sequencing data sample data is traversed, if not, jumping to step 2.1); otherwise ending and exiting.

11. The gene sequencing data compression method as recited in claim 10, wherein the step 2.2) comprises the detailed steps:
2.2.1) sequentially extracting a short string K-mer with respect to the read sequence short string set KR, constructing a positive strand prediction sequence KP1 based on the short string K-mer, wherein any short string K-mer in a read sequence short string set KR has a corresponding tuple (k-mer, 0) in the positive strand prediction sequence KP1, k-mer is the short string K-mer, and 0 indicates supposing the short string K-mer from the positive strand;
2.2.2) obtaining the prediction character c corresponding to every tuple (k-mer, 0) in the positive strand prediction sequence KP1 through the prediction data model P1, P1, so as to obtain a positive strand prediction character sequence PS1 formed by all prediction characters c; the prediction data model P1 contains any short string K-mer in the positive and negative strands of the reference genome and a prediction character c corresponding to the adjacent bit thereof;
2.2.3) sequentially extracting a short string K-mer with respect to the read sequence short string set KR, constructing a negative strand prediction sequence KP2 based on the short string K-mer, wherein any short string K-mer in the read sequence short string set KR has a corresponding tuple (k-mer, 1) in the negative strand prediction sequence KP2, k-mer is the short string K-mer, and 1 indicates supposing the short string K-mer from the negative strand;
2.2.4) obtaining the prediction character c corresponding to the adjacent bit through the prediction data model P1 with respect to every tuple (k-mer, 1) in the negative strand prediction sequence KP2, and obtaining the negative strand prediction character sequence PS2 formed by all prediction characters c;
2.2.5) calculating an editing distance L1 between the positive strand prediction character sequence PS1 and Lr−k bit original gene letter exclusive of k bit original gene letter in the read sequence R, calculating an editing distance L2 between the negative strand prediction character sequence PS2 and the Lr−k bit original gene letter exclusive of k bit original gene letter in the read sequence R;
2.2.6) judging whether the editing distance L1 is less than L2, if yes, determining the type d of the positive and negative strands of the read sequence R to be a positive strand, and the positive strand prediction character sequence PS1 to be the prediction character set PS in Lr−k bit; otherwise, determining the type d of the positive and negative strands of the read sequence R to be negative strand, and the negative strand prediction character sequence PS2 to be the prediction character set PS in Lr−k bit.

12. The gene sequencing data compression method as recited in claim 11, wherein the prediction data model P1 is a gene character string with a length of L, and the step 2.2.2) of obtaining the prediction character c in the adjacent bit thereof corresponding to every tuple (k-mer, 0) in the positive strand prediction sequence KP1 through the prediction data model P1 comprises the following detailed steps:
2.2.2.1) mapping every tuple (k-mer, 0) in the positive strand prediction sequence KP1 to a certain line of an integer set [0, L] using a mapping function corresponding to the prediction data model P1, P1, wherein L is a supremum of the integer set which is as long as the prediction data model P1, P1, and 0 is an infimum of the integer set;

generating a one-dimensional (1D) table T1 with a length of (Lr−k+1) according to a mapping result, wherein the i(th) element T1[i] in the 1D table T1 is respectively and sequentially stored and mapped to a value of the mapping function corresponding to the tuple (k-mer, 0) in the i(th) line of the integer set, i∈[0, Lr−k];

2.2.2.2) obtaining a prediction character c corresponding to the adjacent bit from the prediction data model P1 according to the value of the mapping function corresponding to each tuple of 1D table T1, and generating 1D character sequence PS1, so that the i(th) PS1 [i] value of the 1D character sequence PS1 is equal to the i(th) character P1[T1[i]] in the prediction data model P1, P1, and the i(th) character P1[T1[i]] in the prediction data model P1 is the corresponding character c with the mapping function value of PS1 [i] corresponding to the tuple (k-mer, 0), wherein i∈[0, Lr−k], Lr is a read length of the read sequence R, and k is the length of the short string K-mer.

13. The gene sequencing data compression method as recited in claim 12, wherein the step 2.2.4) of obtaining the prediction character c in the adjacent bit thereof corresponding to every tuple (k-mer, 1) in the negative strand prediction sequence KP2 through the prediction data model P1 comprises the following detailed steps:

2.2.4.1) mapping every tuple (k-mer, 1) in the negative strand prediction sequence KP2 to a certain line of an integer set [0, L] using the mapping function corresponding to the prediction data model P1, P1, wherein L is a supremum of the integer set which is as long as the prediction data model P1, P1, and 0 is an infirnum of the integer set;

generating a 1D table T2 with a length of (Lr−k+1) according to a mapping result, wherein the i(th) element T2[i] in the 1D table T2 is respectively and sequentially stored and mapped to a value of the mapping function corresponding to the tuple (k-mer, 1) in the i(th) line of the integer set, i∈[0, Lr−k];

2.2.4.2) obtaining the prediction character c corresponding to the adjacent bit thereof from the prediction data model P1 thereof according to the value of the mapping function corresponding to each tuple (k-mer, 1) in the 1D table T2, and generating the 1D character sequence PS2, so that the i(th) PS2[i] value of the 1D character sequence PS2 is equal to an i(th) character P1[T2[i]] in the prediction data model P1, P1, wherein the i(th) character P1 [T2[i]] in the prediction data model P1 is the corresponding prediction character c with a mapping function value of PS2[i] corresponding to the tuple (k-mer, 0), i∈[0, Lr−k], Lr is a read length of the read sequence R, and k is the length of the short string K-mer.

14. The gene sequencing data compression method as recited in claim 11, which characterized in that, wherein the prediction data model P1 is a neural network model which is trained in advance based on the short string K-mer in the reference genome and the corresponding base letter $c_0$ in the adjacent bit thereof;

the step 2.2.2) of obtaining the prediction character c in the adjacent bit thereof corresponding to every tuple (k-mer, 0) in the positive strand prediction sequence KP1 through the mapping function of the prediction data model P1 specifically refers to inputting every tuple (k-mer, 0) in the positive strand prediction sequence KP1 into the neural network model to obtain the prediction character c corresponding to the tuple (k-mer, 0);

the step 2.2.4) of obtaining the prediction character c in the adjacent bit thereof corresponding to every tuple (k-mer, 1) in the negative strand prediction sequence KP2 through the prediction data model P1 specifically refers to inputting every tuple (k-mer, 1) in the negative strand prediction sequence KP2 into the neural network model to obtain the prediction character c corresponding to the tuple (k-mer, 1).

15. The gene sequencing data compression method as recited in claim 9, wherein an XOR function or a bit subtraction function is specifically applied for the reversible function in step 2).

16. The gene sequencing data compression method as recited in claim 9, wherein the compression in step 2) specifically refers to a compression using a statistical model and entropy coding.

17. A gene sequencing data compression system, comprising a computer system, wherein the computer system is programmed to perform the steps of the gene sequencing data compression method as recited in claim 9.

18. A non-transitory computer-readable medium on which a computer program is stored, the computer program enables a computer to perform the steps of the gene sequencing data compression method as recited in claim 9.

19. A gene sequencing data decompression method, comprising the following implementation steps:

1) traversing gene sequencing data $data_c$ to be decompressed to obtain a read sequence $R_c$ to be decompressed;

2) with respect to every read sequence Rc to be decompressed, first decompressing and reconstructing the read sequence $R_c$ to be decompressed as a positive and negative strand type d, an original gene sequence CS1 in the k bit and a reversible computing result CS2 with the length of Lr−k bit;

taking the original gene sequence CS1 in the k bit as an initial short string K-mer, and obtaining the corresponding prediction character c in the adjacent bit of the short string K-mer through a preset prediction data model P1, P1, wherein the prediction data model P1 contains any short string K-mer in the positive and negative strands of the reference genome and a corresponding prediction character c in the adjacent bit thereof;

when one prediction character c is obtained, forming a new short string K-mer constituted by new prediction character c and the last k-1 bit of the short string K-mer, obtaining the new prediction character c by the preset prediction data model $P_1$, and eventually obtaining a prediction character set PS with a length of Lr−k bit constituted by all prediction characters c;

performing the reverse computing for the coded reversible computing result CS2 and the prediction character set PS to obtain the decrypted result of the reversible computing result CS2 in the Lr−k bit by virtue of the inverse function of the reversible function;

combining the decrypted results of the original gene sequence CS1 in the k bit and the reversible computing result CS2 to obtain the original read sequence R corresponding to the read sequence Rc to be decompressed, and outputting the original read sequence R.

20. The gene sequencing data decompression method as recited in claim 19, wherein the step 2) comprises the following detailed steps:

2.1) traversing gene sequencing data $data_c$ to be decompressed to obtain a read sequence $R_c$ to be decompressed;

2.2) decompressing and reconstructing the read sequence $R_c$ to be decompressed to be a positive and negative strand type d, an original gene sequence CS1 in the k bit and a reversible computing result CS2 with a length of Lr−k bit;

2.3) taking the original gene sequence CS1 in the k bit as an initial short string K-mer, and obtaining a corresponding prediction character c in the adjacent bit of the short string K-mer through a preset prediction data model P1, P1, wherein the prediction data model P1 contains any short string K-mer in the positive and negative strands of the reference genome and the corresponding prediction character c in the adjacent bit thereof;

when one prediction character c is obtained, forming a new short string K-mer constituted by new prediction character c and the last k-1 bit of the short string K-mer, obtaining the new prediction character c by the preset prediction data model P1, P1, and eventually obtaining a prediction character set PS with a length of Lr−k bit constituted by all prediction characters c;

2.4) performing the reverse computing for the coded reversible computing result CS2 and the prediction character set PS to obtain the decrypted result of the reversible computing result CS2 in the Lr−k bit by virtue of the inverse function of the reversible function;

2.5) combining the decrypted results of the original gene sequence CS1 in the k bit and the reversible computing result CS2 to obtain the original read sequence R corresponding to the read sequence $R_c$ to be decompressed, and outputting the original read sequence R;

2.6) judging whether the read sequence $R_c$ to be decompressed in the gene sequencing data sample $data_c$ to be decompressed is traversed, if not, jumping to step 2.1); otherwise ending and exiting.

21. The gene sequencing data decompression method as recited in claim 20, wherein the step 2.3) comprises the following detailed steps:

2.3.1) creating a window variable CS and a prediction character set PS corresponding to the short string K-mer, setting the initial value of the window variable CS as an original gene sequence CS1 in the k bit, creating an iteration variable j and setting the initial value as 0;

2.3.2) constructing the window variable CS, the type d of positive and negative strands of the read sequence Rc to be decompressed into a tuple (CS, d), mapping the tuple (CS, d) into an integer set [0, 1] by the mapping function, wherein L is the supremum of the integer set and equal to the length of a prediction data model P1; 0 is the infimum of the integer set, and the prediction data model P1 contains any short string K-mer in the positive and negative strands of the reference genome and a prediction character c thereof corresponding to the adjacent bit;

2.3.3) querying the i(th) P1[i] in the prediction data model P1 with the function value obtained from the mapping function, as the prediction character c corresponding to the adjacent bit of the window variable CS, wherein $i \in [0, L]$; assigning the prediction character c to the j(th) bit in the prediction character set PS, wherein $j \in [0, Lr-k]$, and Lr−k is the length of reversible computing result CS2;

2.3.4) after combining the last k-1 bit of the window variable CS and the prediction character c obtained currently, assigning to the window variable CS, and adding 1 to the iteration variable j;

2.3.5) judging whether the iteration variable j is greater than the length (Lr−k) of the reversible computing result CS2, if yes, jumping to the next step, otherwise, jumping to step 2.3.2);

2.3.6) outputting the prediction character set PS with the length of (Lr−k).

22. The gene sequencing data decompression method as recited in claim 21, wherein the step 2.3) comprises the following detailed steps:

S2.3.1) creating a window variable CS and a prediction character set PS corresponding to the short string K-mer, setting the initial value of the window variable CS as the original gene sequence CS1 in the k bit, creating an iteration variable j and setting the initial value as 0;

S2.3.2) inputting the window variable CS to the prediction data model P1 to obtain the prediction character c of the short string K-mer corresponding to the adjacent bit in the positive strand and negative strand of the reference genome, wherein the prediction data model P1 is the neural network model which is trained in advance based on the short string K-mer in the reference genome and the base element $c_0$ corresponding to the adjacent bit thereof;

S2.3.3) assigning the prediction character c to the j(th) bit in the prediction character set PS, wherein $j \in [0, Lr-k]$, and Lr−k is the length of reversible computing result CS2.

S2.3.4) after combining the last k-1 bit of the window variable CS and the prediction character c obtained currently, assigning to the window variable CS, and adding 1 to the iteration variable j;

S2.3.5) judging whether the iteration variable j is greater than the length (Lr−k) of the reversible computing result CS2, if yes, jumping to the next step, otherwise, jumping to step 2.3.2);

S2.3.6) outputting the prediction character set PS with the length of (Lr−k).

23. The gene sequencing data decompression method as recited in claim 19, which characterized in that, wherein the reversible function specifically refers to an XOR function or a bit subtraction function; An inverse function of the XOR function is the XOR operation, and an inverse function of the bit subtraction function is a bit addition function.

24. The gene sequencing data decompression method as recited in claim 19, wherein the decompression and reconstruction in step 2) specifically refer to a decompression and reconstruction using inverse algorithms of a statistical model and entropy coding.

25. A gene sequencing data decompression system based on character prediction, comprising a computer system, wherein the computer system is programmed to perform the steps of the gene sequencing data decompression method as recited in claim 19.

26. A non-transitory computer-readable medium, on which a computer program is stored, the computer program allows the computer to perform the steps of the gene sequencing data decompression method as recited in claim 19.

* * * * *